United States Patent
Lin et al.

(10) Patent No.: US 9,296,731 B2
(45) Date of Patent: Mar. 29, 2016

(54) ANTI-ALLERGY BENZOCYCLOHEPTATHIOPHENE DERIVATIVES

(75) Inventors: Tongjun Lin, Fuzhou (CN); Jun Xin, Dartmouth (CA)

(73) Assignee: Fujian Mindong Rejuvenation Pharmaceutical Co., Ltd., Fujian (CN)

( * ) Notice: Subject to any disclaimer, the term of this patent is extended or adjusted under 35 U.S.C. 154(b) by 0 days.

(21) Appl. No.: 14/129,766

(22) PCT Filed: Jun. 27, 2012

(86) PCT No.: PCT/CN2012/077591
§ 371 (c)(1),
(2), (4) Date: Dec. 27, 2013

(87) PCT Pub. No.: WO2013/000406
PCT Pub. Date: Jan. 3, 2013

(65) Prior Publication Data
US 2014/0135361 A1    May 15, 2014

Related U.S. Application Data

(60) Provisional application No. 61/502,066, filed on Jun. 28, 2011.

(51) Int. Cl.
*C07D 409/14* (2006.01)
*A61K 31/445* (2006.01)

(52) U.S. Cl.
CPC ............ *C07D 409/14* (2013.01); *A61K 31/445* (2013.01)

(58) Field of Classification Search
None
See application file for complete search history.

(56) References Cited

FOREIGN PATENT DOCUMENTS

| CN | 1258219 A | 6/2000 |
|---|---|---|
| EP | 0577325 A1 * | 6/1993 |

(Continued)

OTHER PUBLICATIONS

Crampton, A Comparison of the Relative Clinical Efficacy of a Single Dose of Ketotifen Fumarate 0.025% Ophthalmic Solution Versus Placebo in Inhibiting the Signs and Symptoms of Allergic Rhinoconjunctivitis as Induced by the Conjunctival Allergen Challenge Model, Clinical Therapeutics, 2002, 24(11), pp. 1800-1808.*

(Continued)

*Primary Examiner* — San-Ming Hui
*Assistant Examiner* — Andrew Lee
(74) *Attorney, Agent, or Firm* — Lewis Roca Rothgerber Christie LLP

(57) ABSTRACT

The present invention provides inhibitors of allergy, and allergic reactions specifically compounds of the present invention are described by the following chemical Formula I:

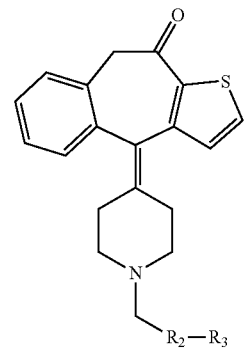

Formula I

A method for treating an allergic reaction, or allergy diseases or disorders includes administering a therapeutically effective composition comprising a compound of Formula I or a pharmaceutically acceptable salt, solvate or prodrug thereof and a pharmaceutically acceptable carrier, vehicle or excipient to a subject in need thereof.

21 Claims, 4 Drawing Sheets

(56) References Cited

FOREIGN PATENT DOCUMENTS

| | | |
|---|---|---|
| EP | 0 577 325 A1 | 1/1994 |
| WO | WO 98/43640 | 10/1998 |

OTHER PUBLICATIONS

International Search Report for Application No. PCT/CN2012/077591, issued Oct. 4, 2012, and English Translation (8 pages).

* cited by examiner

ANTI-ALLERGY BENZOCYCLOHEPTATHIOPHENE DERIVATIVES

CROSS-REFERENCE TO RELATED APPLICATIONS

This application is a National Phase Patent Application and claims priority to and benefit of International Application Number PCT/CN2012/077591, filed on Jun. 27, 2012, which claims priority to and benefit of U.S. Provisional Application No. 61/502,066, filed on Jun. 28, 2011, the entire disclosures of which are incorporated herein by reference.

BACKGROUND

The statements in this section merely provide background information related to the present disclosure and may not constitute prior art.

Allergy is a complex disease. Multiple immune cells and inflammatory mediators contribute to the initiation and manifestation of allergic diseases. In addition to the blockade of histamine H1 receptor, the anti-inflammatory effects have increasingly been recognized to play an important role in the management of allergic diseases. The anti-inflammatory effects include stabilization of mast cells (to prevent mediator release), blockade of lipid mediators such as platelet-activating factor (PAF) and leukotrienes, inhibition of adhesion molecules, and inhibition of eosinophils and CD4 T cells.

Allergic diseases have reached epidemic proportions worldwide. Allergic diseases such as asthma, rhinitis or atopic dermatitis affect at least 8%-16% population with the annual economic burden of 12.7, 1.2, and 3.8 billion dollars, respectively, in the United States and are a major health burden world-wide. The range of allergic diseases includes rhinitis, sinusitis, conjunctivitis, asthma, dermatitis and food allergy. These diseases negatively impact the patient's quality of life and impair their ability to perform in school or workplace. Thus, allergic diseases result in significant socio-economic costs.

Mast cells play a major role in allergy through secretion of granule associated and newly synthesized mediators. They are distributed widely in the body and are especially abundant in skin or mucosa where they can interact with foreign materials such as allergens or pathogens. Mast cells possess a large number of high affinity IgE receptors on their surface. Allergen binding to IgE receptors on mast cells initiates a cascade of signaling events leading to the production of potent inflammatory mediators including histamine, platelet-activating factor, IL-6 and many others.

The role of histamine in the pathophysiology of allergic disorders has been well-recognized. Mast cells produce and store histamine in their granules. Upon allergen activation, mast cells immediately (within seconds) release histamine into local tissues. Histamine exerts its effects in allergic diseases primarily through interacting with histamine H1 receptors which are present in a variety of organs such as nerve endings, blood vessel walls, and airway smooth muscles. Histamine has broad biological effects. Depending on the location where histamine is released, its biological effects vary from mild discomfort of itch to life-threatening bronchoconstriction. In the nose or skin, histamine induces vasodilation and increases vascular permeability leading to edema and erythema. It stimulates the sensory nerve endings leading to itching or sneezing. In the lung, histamine provokes the bronchial smooth muscle leading to bronchoconstriction.

H1 antihistamine agents play a pivotal role in the treatment of allergic diseases and are among the most prescribed medications in the world. Depending on their action on the central nervous system, H1 antihistamines are classified as first-generation and second-generation. In general, first-generation H1 antihistamines such as dexchlorpheniramine, hydroxyzine, contain two features that limit their usage. One, they are rapidly absorbed and metabolized. Thus, they need to be administered 3 to 4 times a day. Second, they are highly lipophilic and easily cross the blood-brain barrier causing a major side effect of sedation. Thus, major efforts have been made to improve H1 antihistamine agents by reducing their side effects on central nervous system and by enhancing the duration of drug effect.

Accordingly, there is a need for newer anti-allergy agents aimed at improved efficacy and reduced side effects.

SUMMARY

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

The invention comprises compounds of Formula I that inhibit histamine and allergic reactions and pharmaceutical compositions thereof. The invention is also directed to methods of inhibiting allergic hypersensitivity and for treating allergy, or allergic conditions or diseases in a subject in need thereof.

A first aspect of the invention provides a compound of Formula I:

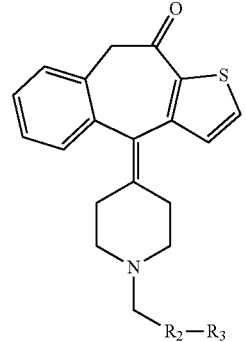

Formula I or a pharmaceutically acceptable salt, solvate or prodrug thereof, wherein $R_2$ is each independently $C_{1-8}$ alkyl, $C_{2-8}$ alkenyl, $C_{2-8}$ alkynyl, alkoxy, alkenoxy, $C_{4-10}$ cycloalkyl, $C_{4-10}$ heterocycloalkyl, $C_{4-10}$ aryl, $C_{4-10}$ aralkyl, aralkyloxy, $C_{4-10}$ heteroaryl, or $C_{4-10}$ heteroaralkyl, wherein each $C_{1-8}$ alkyl, $C_{2-8}$ alkenyl, $C_{2-8}$ alkynyl, alkoxy, alkenoxy, $C_{4-10}$ cycloalkyl, $C_{4-10}$ heterocycloalkyl, $C_{4-10}$ aryl, $C_{4-10}$ aralkyl, aralkyloxy, $C_{4-10}$ heteroaryl, or $C_{4-10}$ heteroaralkyl optionally including 1-3 substituents independently selected from $Q_1$ or $Q_2$;

$R_3$ is each independently, hydrogen, halo, OH, —CN, —NO$_2$, —N═O, —NHOQ$_1$, —OQ$_1$, —SOQ$_1$, —SO$_2$Q$_1$, —SON(Q$_1$)$_2$, —SO$_2$N(Q$_1$)$_2$, —N(Q$_1$)$_2$, —C(O)OQ$_1$, —C(O)Q$_1$, —C(O)N(Q$_1$)$_2$, —C(═NQ$_1$)NQ$_1$-, —NQ$_1$C (=NQ$_1$)NQ$_1$-, —C(O)N(Q$_1$)(OQ$_1$), —N(Q$_1$)C(O)-Q$_1$, —N(Q$_1$)C(O)N(Q$_1$)$_2$, —N(Q$_1$)C(O)O-Q$_1$, —N(Q$_1$)SO$_2$Q$_1$, —N(Q$_1$)SOQ$_1$, C$_{1-8}$ alkyl, C$_{2-8}$ alkenyl, C$_{2-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, or C$_{4-10}$ heteroaralkyl, wherein each C$_{1-8}$ alkyl, C$_{2-8}$ alkenyl, C$_{2-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, or C$_{4-10}$ heteroaralkyl optionally substituted with 1-3 substituents independently selected from Q$_1$ or Q$_2$;

each Q$_1$ is independently hydrogen, C$_{1-8}$ alkyl, C$_{2-8}$ alkenyl, alkoxy, alkenoxy, C$_{4-10}$ cycloalkyl, C$_{4-10}$ aryl, C$_{4-10}$ arylalkyl, aralkyloxy, C$_{4-10}$ heterocyclic, or C$_{4-10}$ heteroaryl ring, each optionally including 1-3 substituents independently selected from Q$_2$;

each Q$_2$ is halo, haloalkyl, oxo, oxime, azido, amino, amido, cyano, ON, NO$_2$, CF$_3$, OCF$_3$, OH, —COOH or C$_1$-C$_4$ alkyl optionally substituted with 1-3 of halo, oxo, oxime, —ON, —NO$_2$, —CF$_3$, —OCF$_3$, —OH, —SH, —S(O)$_3$H, —NH$_2$, or —COOH.

The R$_2$ Variable

In some embodiments, R$_2$ is each independently C$_{1-8}$ alkyl, C$_{1-8}$ alkenyl, C$_{1-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, or C$_{4-10}$ heteroaralkyl, wherein each C$_{1-8}$ alkyl, C$_{1-8}$ alkenyl, C$_{1-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, or C$_{4-10}$ heteroaralkyl optionally substituted with 1-3 substituents independently selected from hydrogen, C$_{1-8}$ alkyl, C$_{1-8}$ alkenyl, alkoxy, alkenoxy, cycloalkyl, heterocycloalkyl, aryl, arylalkyl, aralkyloxy, or heteroaryl, wherein each C$_{1-8}$ alkyl, C$_{1-8}$ alkenyl, alkoxy, alkenoxy, cycloalkyl, heterocycloalkyl, aryl, arylalkyl, aralkyloxy, or heteroaryl optionally including 1-3 substituents independently selected from halo, oxo, oxime, azido, amino, amido, cyano, ON, NO$_2$, CF$_3$, OCF$_3$, OH, —COOH or C$_1$-C$_4$ alkyl optionally substituted with 1-3 of halo, oxo, oxime, —ON, —NO$_2$, —CF$_3$, —OCF$_3$, —OH, —SH, —S(O)$_3$H, —NH$_2$, or —COOH. In another aspect, R$_2$ is C$_{1-8}$ alkyl, C$_{1-8}$ alkenyl, C$_{4-10}$ cycloalkyl, C$_{4-10}$ heterocycloalkyl, C$_{4-10}$ aryl, or C$_{4-10}$ heteroaryl. In another aspect, R$_2$ is C$_{4-10}$ cycloalkyl, C$_{4-10}$ heterocycloalkyl or C$_{4-10}$ heteroaryl. In some aspects, R$_2$ is a C$_{4-10}$ heterocycloalkyl or C$_{4-10}$ heteroaryl.

In some aspects, R$_2$ is piperidine, pyridine, azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl. pyridine-N-oxide, 1-piperidinyl, 2-piperidinyl, 3-piperidinyl, 4-piperidinyl, N-methyl-piperidinyl, N-ethyl-piperidinyl, N-propyl-piperidinyl, hexahydrothiopyranyl, azepanyl, methylazepanyl, tetrahydropyranyl, piperidinylmethyl, pyridinyl, pyridinylmethyl, tetrahydrothiopyranyl, dioxolanylmethyl, dioxanylmethyl. N-isopropyl-piperidinyl, N-butyl-piperidinyl, N-pentyl-piperidinyl, N-hexylpiperidinyl, N-cyclohexyl-piperidinyl, N-acetyl-piperidinyl, or N-benzyl-piperidinyl. In some aspects, R$_2$ is pyridine.

The R$_3$ Variable

In some embodiments, R$_3$ is each independently hydrogen, halo, OH, —CN, —NO$_2$, —N=O, —NHOQ$_1$, —OQ$_1$, —SOQ$_1$, —SO$_2$Q$_1$, —SON(Q$_1$)$_2$, —SO$_2$N(Q$_1$)$_2$, —N(Q$_1$)$_2$, —C(O)OQ$_1$, —C(O)Q$_1$, —C(O)N(Q$_1$)$_2$, —C(=NQ$_1$)NQ$_1$-, —NQ$_1$C(=NQ$_1$)NQ$_1$-, —C(O)N(Q$_1$)(OQ$_1$), —N(Q$_1$)C(O)-Q$_1$, —N(Q$_1$)C(O)N(Q$_1$)$_2$, —N(Q$_1$)C(O)O-Q$_1$, —N(Q$_1$)SO$_2$Q$_1$, —N(Q$_1$)SOQ$_1$, C$_{1-8}$ alkyl, C$_{2-8}$ alkenyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, C$_{4-10}$ heteroaralkyl, wherein each C$_{1-8}$ alkyl, C$_{2-8}$ alkenyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, C$_{4-10}$ heteroaralkyl optionally substituted with 1-3 substituents independently selected from halo, haloalkyl, oxo, oxime, azido, amino, amido, cyano, CN, NO$_2$, CF$_3$, OCF$_3$, OH, —COOH or C$_1$-C$_4$ alkyl optionally substituted with 1-3 of halo, oxo, oxime, —CN, —NO$_2$, —CF$_3$, —OCF$_3$, —OH, —SH, —S(O)$_3$H, —NH$_2$, or —COOH.

each Q$_1$ is independently hydrogen, C$_{1-8}$ alkyl, C$_{2-8}$ alkenyl, alkoxy, alkenoxy, C$_{4-10}$ cycloalkyl, C$_{4-10}$ aryl, C$_{4-10}$ arylalkyl, aralkyloxy, C$_{4-10}$ heterocyclic, or C$_{4-10}$ heteroaryl ring, each optionally including 1-3 substituents independently selected from Q$_2$;

each Q$_2$ is halo, haloalkyl, oxo, oxime, azido, amino, amido, cyano, CN, NO$_2$, CF$_3$, OCF$_3$, OH, —COOH or C$_1$-C$_4$ alkyl optionally substituted with 1-3 of halo, oxo, oxime, —CN, —NO$_2$, —CF$_3$, —OCF$_3$, —OH, —SH, —S(O)$_3$H, —NH$_2$, or —COOH. In some aspects, R$_3$ is each independently selected from H, C$_{1-8}$ alkyl, C$_{1-8}$ alkenyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, C$_{4-10}$ heteroaralkyl. In another aspect, R$_3$ is H or C$_{1-8}$ alkyl. In another aspect, R$_3$ is hydrogen, methyl, ethyl, propyl, isopropyl, butyl, isobutyl, hexyl, 2-ethylpropyl, and cyclohexyl. In some aspects, R$_3$ is hydrogen or methyl.

In a second aspect, the invention is directed to a pharmaceutical composition which comprises a compound of Formula I or a pharmaceutically acceptable salt thereof and a pharmaceutically acceptable carrier, excipient, or diluent.

In a third aspect, the invention comprises a method of inhibiting an allergic response, for example, an anti-histamine response, stabilization of mast cells (to prevent mediator release), blockade of lipid mediators such as platelet-activating factor (PAF) and leukotrienes, inhibition of adhesion molecules and inhibition of eosinophils and inhibition of CD4 T-cell cytotoxicity, the method comprising contacting a cell with a compound of Formula I or a pharmaceutically acceptable salt or solvate thereof, or with a pharmaceutical composition comprising a therapeutically effective amount of a compound of Formula I and a pharmaceutically acceptable carrier, excipient, or diluent.

In a fourth aspect, the invention provides a method for treating an allergic disease, disorder, or syndrome, the method comprising administering to a subject a pharmaceutical composition comprising a therapeutically effective amount of a compound of Formula I or a pharmaceutically acceptable salt or solvate thereof, or a pharmaceutical composition comprising a therapeutically effective amount of a compound of Formula I and a pharmaceutically acceptable carrier, excipient, or diluent.

In a further aspect, the present invention provides an ophthalmic composition comprising a compound of formula I and an ophthalmic acceptable excipient, carrier or vehicle.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1A:
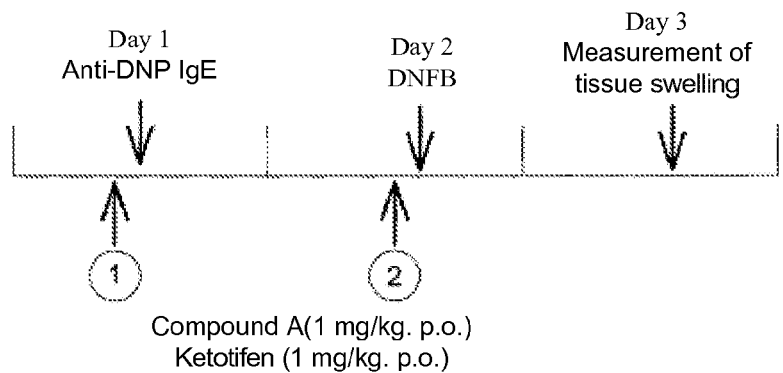
FIG. 1A depicts the treatment schedule for allergy testing in vivo using dinitrofluorobenzene (DNFB) and inhibition of allergic responses with ketotifen and Compound A in mice.

The following description is merely exemplary in nature and is not intended to limit the present disclosure, application, or uses.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present technology, and are not intended to limit the disclosure of the present technology or any aspect thereof. In particular, subject matter disclosed in the "Introduction" may include novel technology and may not constitute a recitation of present technology. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are present technology or have any relevance to the patentability of the technology disclosed herein. Any discussion of the content of references cited in the Introduction is intended merely to provide a general summary of assertions made by the authors of the references, and does not constitute an admission as to the accuracy of the content of such references. All references cited in the "Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1.1-9.9, 1-8, 1-3, 1-2, 2-10, 2-8, 2-3, 3-10, and 3-9.

Although the open-ended term "comprising," as a synonym of terms such as including, containing, or having, is used herein to describe and claim the present invention, the invention, or embodiments thereof, may alternatively be described using more limiting terms such as "consisting of" or "consisting essentially of" the recited ingredients.

ABBREVIATIONS AND DEFINITIONS

The following abbreviations and terms have the indicated meanings throughout:

| Abbreviation | Meaning |
| --- | --- |
| br | broad |
| ° C. | degrees Celsius |
| CBZ | CarboBenZoxy = benzyloxycarbonyl |
| d | doublet |
| dd | doublet of doublet |
| dt | doublet of triplet |
| EI | Electron Impact ionization |
| Et | Ethyl |
| g | gram(s) |
| GC | gas chromatography |
| h or hr | hour(s) |
| HPLC | high pressure liquid chromatography |
| L | liter(s) |
| M | molar or molarity |
| m | Multiplet |
| Me | Methyl |
| mg | milligram(s) |
| MHz | megahertz (frequency) |
| Min | minute(s) |
| mL | milliliter(s) |
| mM | Millimolar |
| mmol | millimole(s) |
| mol | mole(s) |
| MS | mass spectral analysis |
| N | normal or normality |
| nM | Nanomolar |
| NMR | nuclear magnetic resonance spectroscopy |
| p.o. | per Oral |
| q | Quartet |
| RT | Room temperature |
| s | Singlet |
| s- | Secondary |
| t- | Tertiary |
| t or tr | Triplet |
| TFA | trifluoroacetic acid |
| THF | Tetrahydrofuran |
| µL | microliter(s) |
| µM | Micromole(s) or micromolar |

The symbol "—" means a single bond, "═" means a double bond, "≡" means a triple bond, and "---" means a single bond and optionally a double bond. When chemical structures are depicted or described, unless explicitly stated otherwise, all carbons are assumed to have hydrogen substitution to conform to a valence of four.

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., anti-histamine, anti-inflammatory, antibiotic, etc.), "administration" and its variants are each understood to include concurrent and sequential introduction of the compound or prodrug thereof and other agents.

If a group "R" is depicted as "floating" on a ring system, as for example in the Formula:

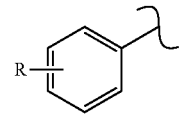

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused or bridged ring system, as for example in the Formula e:

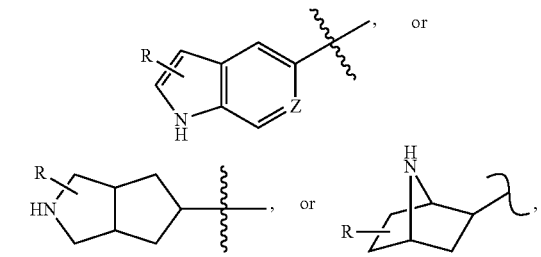

then, unless otherwise defined, a substituent "R" may reside on any atom of the fused or bridged ring system, assuming replacement of a depicted hydrogen (for example the —NH— in the Formula above), implied hydrogen (for example as in the Formula above, where the hydrogens are not shown but understood to be present), or expressly defined hydrogen (for example where in the Formula above, "Z" equals ═CH—) from one of the ring atoms, so long as a stable structure is formed. In the example depicted, the "R" group may reside on either the 5-membered or the 6-membered ring of the fused or bridged ring system.

When a group "R" is depicted as existing on a ring system containing saturated carbons, as for example in the Formula:

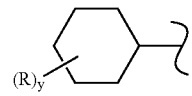

where, in this example, "y" can be more than one, assuming each replaces a currently depicted, implied, or expressly defined hydrogen on the ring; then, unless otherwise defined, where the resulting structure is stable, two "R's" may reside on the same carbon. In another example, two R's on the same carbon, including that carbon, may form a ring, thus creating a spirocyclic ring structure with the depicted ring as for example in the Formula:

"Alkenyl" or "lower alkenyl" means a straight or branched hydrocarbon radical having from 2 to 8 carbon atoms and at least one double bond and includes ethenyl, propenyl, 1-but-3-enyl, 1-pent-3-enyl, 1-hex-5-enyl and the like.

"Alkenylcarbonyl" means a C(O)R group where R is alkenyl, as defined herein.

"Alkenyloxy" or "lower alkenyloxy" means an —OR group where R is alkenyl, as defined herein. Representative examples include methoxy, ethoxy, 1-methoxyprop-1-en-3-yl, propoxy, isopropoxy, cyclopropyloxy, cyclohexyloxy and the like.

"Alkoxy" or "lower alkoxy" means an —OR group where R is alkyl, as defined herein. Representative examples include methoxy, ethoxy, 1-methoxyprop-1-en-3-yl, propoxy, isopropoxy, cyclopropyloxy, cyclohexyloxy and the like.

"Alkoxyalkyl" means an alkyl group, as defined herein, substituted with one, two, or three alkoxy groups, as defined herein.

"Akoxycarbonyl" means a —C(O)OR group where R is alkyl as defined herein.

"Alkoxycarbonylalkyl" means an alkyl group, as defined herein, substituted with one, two, or three alkoxycarbonyl groups, as defined herein.

"Alkyl" or "lower alkyl" means a linear or branched hydrocarbon group having one to eight carbon atoms. Examples of lower alkyl groups include methyl, ethyl, propyl, isopropyl, butyl, s-butyl, t-butyl, isobutyl, pentyl, hexyl, heptyl, octyl and the like. A "$C_0$" alkyl (as in "$C_0$-$C_6$-alkyl") is a covalent bond. "$C_6$ alkyl" refers to, for example, n-hexyl, iso-hexyl, and the like.

"Alkylamino" means a —NHR radical where R is alkyl as defined herein, or an N-oxide derivative thereof, e.g., methylamino, ethylamino, n-, iso-propylamino, n-, iso-, tert-butylamino, or methylamino-N-oxide, and the like.

"Alkylaminoalkyl" means an alkyl group substituted with one or two alkylamino groups, as defined herein.

"Alkylaminoalkyloxy" means an —OR group where R is alkylaminoalkyl, as defined herein.

"Alkylcarbonyl" means a C(O)R group where R is alkyl, as defined herein.

"Alkylcarbonylamino" means a —NRC(O)R' group where R is hydrogen or alkyl, as defined herein, and R' is alkyl, as defined herein.

"Alkylene" refers to straight or branched divalent hydrocarbon, containing no unsaturation and having from two to eight carbon atoms. Examples of alkylene include eth-diyl (—$CH_2CH_2$—), prop-1,3-diyl (—$CH_2CH_2CH_2$—), 2,2-dimethylprop-1,3-diyl (—$CH_2C(CH_3)_2CH_2$—), and the like.

"Alkylsulfonyl" means a —$S(O)_2R$ group where R is alkyl, as defined herein.

"Alkylthio" means a —SR group where R is alkyl, as defined herein. Examples of alkylthio include methylthio and ethylthio, and the like.

"Alkylthioalkyl" means an alkyl group substituted with one or two alkylthio groups, as defined herein, e.g. 2-(methylthio)-ethyl and 2-(ethylthio)-ethyl.

"Alkynyl" or "lower alkynyl" means a straight or branched hydrocarbon radical having from 2 to 6 carbon atoms and at least one triple bond and includes ethynyl, propynyl, butynyl, pentyn-2-yl and the like.

"Amino" means a —$NH_2$.

"Aminoalkyl" means an alkyl group substituted with at least one, specifically one, two, or three, amino groups.

"Aminoalkyloxy" means an —OR group where R is aminoalkyl, as defined herein.

"Aryl" means a monovalent six- to fourteen-membered, mono- or bi-carbocyclic ring, wherein the monocyclic ring is aromatic and at least one of the rings in the bicyclic ring is aromatic. Representative examples include phenyl, naphthyl, and indanyl, and the like.

"Arylalkyl" means an alkyl group, as defined herein, substituted with one or two aryl groups, as defined herein. Examples include benzyl, phenethyl, phenylvinyl, phenylallyl and the like.

"Aryloxy" means a —OR group where R is aryl as defined herein.

"Arylalkyloxy" means a —OR group where R is arylalkyl as defined herein.

"Arylsulfonyl" means a —$SO_2R$ group where R is aryl as defined herein.

"Carboxyalkyl" means an alkyl group, as defined herein, substituted with one, two, or three —C(O)OH groups.

"Carboxy ester" means a —C(O)OR group where R is lower alkyl, lower alkenyl, lower alkynyl, cycloalkyl, aryl or arylalkyl, each of which is defined herein. Representative examples include methoxycarbonyl, ethoxycarbonyl, and benzyloxycarbonyl, and the like.

"Cyanoalkyl" means an alkyl, alkenyl, or alkynyl radical, as defined herein, substituted with at least one, specifically one, two, or three, cyano groups.

"Cycloalkyl" means a monocyclic or polycyclic hydrocarbon radical having three to thirteen carbon atoms. The cycloalkyl can be saturated or partially unsaturated, but cannot contain an aromatic ring. Cycloalkyl includes fused, bridged, and spiro ring systems. Examples of such radicals include cyclopropyl, cyclobutyl, cyclopentyl and cyclohexyl.

"Cycloalkylalkyl" means alkyl group substituted with one or two cycloalkyl group(s), as defined herein. Representative examples include cyclopropylmethyl and 2-cyclobutyl-ethyl, and the like.

"Cycloalkylcarbonyl" means a —C(O)R group where R is cycloalkyl as defined herein.

"Dialkylamino" means a —NRR' radical where R and R' are independently alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with one or dialkylamino group(s), as defined herein.

"Dialkylaminoalkyloxy" means an —OR group where R is dialkylaminoalkyl, as defined herein.

"Fused ring system" and "fused ring" refer to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydronaphthalene. A spiro ring system is not a fused-polycyclic by this definition, but fused polycyclic ring systems of the invention may themselves have spiro rings attached thereto via a single ring atom of the fused-polycyclic. In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Haloaloxy" means an —OR' group where R' is haloalkyl as defined herein, e.g., trifluoromethoxy or 2,2,2-trifluoroethoxy, and the like.

"Haloalkoxyalkyl" means an alkyl group, as defined herein, substituted with one, two, or three haloalkoxy, as defined herein.

"Halogen" or "halo" means fluoro, chloro, bromo and iodo.

"Haloalkenyl means an alkenyl group, as defined herein, substituted with one or more halogens, specifically one to five halo atoms.

"Haloalkyl" means an alkyl group, as defined herein, substituted with one or more halogens, specifically one to five halo atoms. Representative examples includes 2,2-difluoroethyl, trifluoromethyl, and 2-chloro-1-fluoroethyl, and the like.

"Heteroaryl" means a monocyclic, fused bicyclic, or fused tricyclic, monovalent radical of 5 to 14 ring atoms containing one or more, specifically one, two, three, or four ring heteroatoms independently selected from —O—, —S(O)$_n$— (n is 0, 1, or 2), —N—, —N(R$^x$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^x$ is hydrogen, alkyl, hydroxy, alkoxy, acyl, or alkylsulfonyl. Fused bicyclic radical includes bridged ring systems. Unless stated otherwise, the valency may be located on any atom of any ring of the heteroaryl group, valency rules permitting. In particular, when the point of valency is located on the nitrogen, R$^x$ is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, or N-oxide or a protected derivative thereof.

"Hetereoarylalkyl" means an alkyl group substituted with one or two heteroaryl group(s) as defined herein.

"Heterocycloalkyl" means a saturated or partially unsaturated monocyclic group of 3 to 8 ring atoms or a saturated or partially unsaturated monovalent fused bicyclic group of 5 to 10 ring atoms in which one or more, specifically one, two, three, or four ring heteroatoms independently selected from —O—, —S(O)$_n$— (n is 0, 1, or 2), —N=, —N(R$^y$)— (where R$^y$ is hydrogen, alkyl, hydroxy, alkoxy, acyl, or alkylsulfonyl), the remaining ring atoms being carbon. Heterocycloalkyl is also known as heterocycle. One or two ring carbon atoms may be replaced by a —C(O)—, —C(S)—, or —C(=NH)— group. Fused bicyclic radical includes bridged ring systems. Unless otherwise stated, the valency of the group may be located on any atom of any ring within the radical, valency rules permitting. In particular, when the point of valency is located on a nitrogen atom, R$^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, and the derivatives thereof and N-oxide or a protected derivative thereof.

"Heterocycloalkylalkyl" means an alkyl group, as defined herein, substituted with one or two heterocycloalkyl group(s), as defined herein.

"Hydroxyalkyl" means an alkyl radical, as defined herein, substituted with at least one, specifically one, two, or three, hydroxy group(s), provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, specifically 2-hydroxyethyl, 2,3-dihydroxypropyl, or 1-(hydroxymethyl)-2-hydroxyethyl, and the like.

"Hydroxyamino" means a —NH(OH) group.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted aryl C$_{1-8}$ alkyl," both the "C$_{1-8}$ alkyl" portion and the "aryl" portion of the molecule may or may not be substituted. A list of exemplary optional substitutions is presented below in the definition of "substituted."

"Optionally substituted alkyl" means an alkyl radical, as defined herein, optionally substituted with one or more group(s), specifically one, two, three, four, or five groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, carboxy, alkylcarbonylamino, alkylcarbonyloxy, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, alkyl, optionally substituted alkenyl, optionally substituted alkynyl, hydroxy, alkoxy, alkenyloxy, or cyanoalkyl), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —C(O)NR$^a$R$^b$ (where R$^a$ and R$^b$ are independently hydrogen, alkyl, optionally substituted alkenyl, optionally substituted alkynyl, hydroxy, alkoxy, alkenyloxy, or cyanoalkyl).

"Optionally substituted alkenyl" means an alkenyl radical, as defined herein, optionally substituted with one or more group(s), specifically one, two, or three groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, carboxy, alkylcarbonylamino, alkylcarbonyloxy, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, optionally substituted alkyl, optionally substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —C(O)NR$^a$R$^b$ (where R$^a$ and R$^b$ are independently hydrogen, optionally substituted alkyl, alkenyl, optionally substituted alkynyl, hydroxy, alkoxy, or alkenyloxy).

"Optionally substituted aryl" means an aryl group, as defined herein, which is optionally substituted with one, two, three, four, of five groups selected from halo, haloalkyl, haloalkoxy, hydroxy, lower alkyl, lower alkenyl, lower alkynyl, alkoxy, carboxy, carboxy ester, amino, alkylamino, dialkylamino, optionally substituted cycloalkyl, optionally substituted heterocycloalkyl, optionally substituted heteroaryl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), and —NHS(O)$_2$R' (where R' is alkyl, aryl, or heteroaryl).

"Optionally substituted heteroaryl" means a heteroaryl group, as defined herein, optionally substituted with one, two, three, four, or five groups selected from halo, haloalkyl, haloalkoxy, lower alkyl, lower alkenyl, lower alkynyl, alkoxy, hydroxy, oxo (valency rules permitting), carboxy, carboxy ester, amino, alkylamino, dialkylamino, optionally substituted cycloalkyl, optionally substituted heterocycloalkyl, heteroaryl, optionally substituted aryl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), and —NHS(O)$_2$R' (where R' is alkyl, aryl, or heteroaryl).

"Optionally substituted heterocycloalkyl" means a heterocycloalkyl, as defined herein, optionally substituted with one, two, three, four, or five groups selected from halo, haloalkyl, haloalkoxy, hydroxy, oxo, oxime, lower alkyl, lower alkenyl, lower alkynyl, alkoxy, optionally substituted cycloalkyl, heterocycloalkyl, optionally substituted aryl, optionally substituted heteroaryl, alkylaminoalkyl, dialkylaminoalkyl, carboxy, carboxy ester, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), amino, alkylamino, dialkylamino, and —NHS(O)$_2$R' (where R' is alkyl, aryl, or heteroaryl).

"Preventing" or "prevention" of a disease, disorder, or syndrome includes inhibiting the disease from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome.

"Treating" or "treatment" of a disease, disorder, or syndrome, as used herein, includes (i) inhibiting the disease, disorder, or syndrome, i.e., arresting its development; and (ii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art. Treatment as a prophylactic measure is also included. Treatment includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs and the like), surgery; radiation therapy; and gene therapy.

"Co-administration" or "combined administration" or the like as utilized herein are meant to include modes of administration of the selected active, therapeutic agents to a single patient, and are intended to include treatment regimens in which the agents are not necessarily administered by the same route of administration or at the same time. Co-administration can also include delivery of the active ingredients in a "fixed combination," e.g. a Compound of Formulae I and an anti-inflammatory agent, which are both administered to a patient simultaneously in the form of a single entity or dosage. The term "non-fixed combination" means that the active ingredients, e.g. a Compound of Formula I and a second active agent, for example, an anti-inflammatory agent as exemplified below, are both administered to a patient as separate entities either simultaneously, concurrently or sequentially with no specific time limits, such that the administration provides therapeutically effective levels of the combination of active agents in the body of the patient.

For the purposes of the present invention, the terms "Subject" or "Patient" which are used interchangeably herein, include humans and other animals, particularly mammals, and other organisms. Thus the methods are applicable to both human therapy and veterinary applications. In a specific embodiment the patient is a mammal, and in a more specific embodiment the patient is human.

"Hypersensitivity and/or disorders related to immune hypersensitivity generally refer to allergic forms of a disease exemplified but not limited to: asthma, rhinitis, conjunctivitis, rhinoconjuctivitis, dermatitis, urticaria, food hypersensitivity, drug hypersensitivity, insect sting or bite hypersensitivity, and anaphylaxis. In particular, hypersensitivity also includes any type of allergy.

As used herein, "allergy" encompasses "allergic hypersensitivity" and is to be understood as suggested by Johansson et al. 2001, Allergy 56:813-824 and Johannson et al. 2004, J. Allergy Clin. Immunol. 113(5) 832-835. Unless otherwise indicated, the application follows the nomenclature for allergy as set forth therein. Allergy or allergic hypersensitivity is a hypersensitivity reaction initiated by immunologic mechanisms in response to a substance (allergen), often in a genetically predisposed individual (atopy). Allergy can be antibody- or cell-mediated. In most patients, the antibody typically responsible for an allergic reaction belongs to the IgE isotype (see "antibodies") and these patients may be said to suffer from IgE-mediated allergy (type-I allergy). It must be noted that not all IgE-mediated allergic reactions occur in atopic subjects. In non IgE-mediated allergy, the antibody may belong to the IgG isotype. Thus, within the meaning of the application, "allergy" refers to both, IgE-mediated allergy (type-I allergy) and non IgE-mediated allergy. IgE-mediated allergy is preferably addressed by the invention. Therefore, in the context of the invention allergy preferably refers to IgE-mediated allergy. Allergies are classified according to the source of the antigen evoking the hypersensitive reaction. In one embodiment allergy is selected from (a) food allergy, (b) drug allergy, (c) house dust allergy, (d) insect venom or bite allergy, and (e) pollen allergy. Alternatively, allergies are classified based on the major symptoms of the hypersensitive reaction. Thus, in another embodiment allergy refers to any allergic form of a disease including, but not limited to: asthma, rhinitis, conjunctivitis, rhinoconjuctivitis, dermatitis, urticaria and anaphylaxis.

As used herein, "type-I allergy": the terms "type-I allergy" and "IgE-mediated allergy" are used interchangeably and relate to IgE-mediated hypersensitivities to allergens. Preferred embodiments of the invention relate to IgE-mediated allergy exemplified by pollen allergy (hay fever); house dust allergy; food allergy; drug allergy; insect venom or bite allergy, preferably bee venom allergy; and animal allergy, preferably cat allergy.

As used herein, "hay fever" is encompassed by a typical form of an IgE-mediated allergy (type-I allergy) against pollen which may comprise rhinitis, conjunctivitis and/or asthma, wherein asthma preferably occurs in chronic forms of hay fever.

As used herein, "atopy", "atopic diseases": Atopy is a personal or familial tendency to produce IgE antibodies in response to low doses of allergens, usually proteins, and to develop typical symptoms such as asthma, rhinoconjunctivitis, or eczema/dermatitis. The first manifestations of atopy in a child are often allergic symptoms, such as diarrhea, wheezing, and skin rashes, and only later can the responsible IgE antibody be detected. Allergic symptoms in a typical atopic individual may be referred to as atopic. In one embodiment of the invention hypersensitivity is an atopic disease, preferably an atopic disease selected from the group consisting of (a) atopic asthma, (b) atopic eczema, (c) atopic IgE-mediated allergy, preferably pollen allergy (hay fever), house dust allergy or house dust mite allergy. In one embodiment the application relates to IgE-mediated allergy in general, irrespective of whether or not said IgE-mediated allergy is regarded as atopic or non atopic allergy. However, specifically preferred embodiments of the invention relate to atopic allergy, preferably to IgE-mediated atopic allergy.

As used herein, "rhinitis" relates to hypersensitivity symptoms from the nose, for example, itching, sneezing, increased secretion, and blockage. Rhinitis relates to non-allergic as well as allergic, i.e. immunologically mediated, rhinitis. Preferred embodiments of the invention relate to allergic rhinitis, preferably to IgE-mediated and non IgE-mediated forms of allergic rhinitis. Specifically preferred embodiments relate to IgE-mediated allergic rhinitis.

As used herein, the term "conjunctivitis" relates to primarily irritations of the eye which can be of allergic as well as non-allergic origin, wherein allergic conjunctivitis encompasses IgE-mediated and non IgE-mediated allergic conjunctivitis. Allergic conjunctivitis, especially IgE mediated allergic conjunctivitis is commonly accompanied by allergic rhinitis, so this disorder is appropriately termed allergic rhinoconjuctivitis. Besides IgE-mediated conjunctivitis, contact allergic conjunctivitis involving TH1 mechanisms occurs. Non-allergic conjunctivitis also often accompanies non-allergic rhinitis. In some embodiments of the invention, conjunctivitis may relate to allergic conjunctivitis, including IgE-mediated and non IgE-mediated forms of allergic conjunctivitis. In one embodiment, the present invention relates to IgE-mediated allergic conjunctivitis. Other embodiments relate to IgE-mediated allergic rhinoconjunctivitis.

As used herein, "asthma" or asthma bronchiale is a chronic respiratory disease due to inflammation of the air passages in the lungs and affects the sensitivity of the nerve endings in the airways so they become easily irritated. Asthma is intended to encompass bronchial asthma, allergic asthma, intrinsic asthma, and occupational asthma. In an asthma attack, the lining of the passages swell causing the airways to narrow and reducing the flow of air in and out of the lungs. Asthma can occur in a intermittent form (2 attacks per week or less during daytime, 2 attacks per month or less at night), in persistent form (permanent attacks during daytime, frequent attacks at night) and in any intermediate form. Within the meaning of the present invention, the term asthma may relate to non-allergic as well as to allergic asthma. In some embodiments of the invention, asthma may relate to allergic asthma, including IgE-mediated and non IgE-mediated forms of asthma. Other embodiments relate to IgE-mediated allergic asthma, for example, to atopic asthma.

As used herein, "atopic asthma" includes IgE-mediated form of asthma in patients with a genetic predisposition which often occurs in conjunction with atopic eczema and IgE-mediated allergies, for example pollen allergy (hay fever), house dust or dust mite.

As used herein, "dermatitis" relates to local inflammation of the skin and encompasses, besides other forms, "eczema" and "contact dermatitis". In some embodiments of the invention, dermatitis may encompass eczema and contact dermatitis.

As used herein, the term "eczema" relates to the atopic eczema/dermatitis syndrome (AEDS), describing an aggregation of several skin diseases with certain clinical characteristics in common involving a genetically determined skin barrier defect. This genetically determined target organ sensitivity constitutes the basis for eczema. In children and young adults of the atopic constitution, the underlying inflammation is dominated by an IgE-antibody associated reaction (atopic eczema). In chronic cases, the inflammation seems to be less influenced by IgE antibody, and the dominating cells in biopsies are lymphocytes. Eczema relates to non-allergic eczema and allergic eczema. In some embodiments of the invention, eczema includes allergic eczema including atopic (IgE-mediated) eczema and non-atopic forms of eczema. In some embodiments, the invention relates to atopic (IgE-mediated) eczema.

As used herein, the term "contact dermatitis" relates to local inflammatory reaction in the skin caused by close contact with low molecular weight chemicals or irritants. Contact dermatitis can be of allergic as well as non-allergic nature. Allergic contact dermatitis is mediated by immunological mechanisms, predominantly TH1 lymphocytes. Typical allergens acting as haptens and causing allergic contact dermatitis can include: nickel, chromium ions, fragrances, preservatives, and urushiol, from the poison ivy plant among others. Exposure can occur through oral uptake, so-called systemic allergic contact dermatitis. A subgroup of contact dermatitis, protein contact dermatitis, is an IgE-associated reaction caused by absorption of proteins through damaged skin. In some embodiments of the invention, contact dermatitis includes allergic contact dermatitis. Further embodiments relate to protein contact dermatitis.

As used herein, the term "urticaria" relates to a non inflammatory reaction in the skin caused by an irritant or allergen and includes non-allergic urticaria as well as allergic urticaria. Allergic urticaria is mediated by immunological mechanisms, which commonly is IgE-mediated but can also be immune complex-associated. Urticaria can also develop locally after topical contact with the allergen, as occurs on the hands of a person with latex allergy wearing latex gloves or in a person with dog allergy licked by a dog. In some embodiments of the invention, the term urticaria relates to allergic urticaria, most preferably IgE-mediated allergic urticaria.

As used herein, "food hypersensitivity" includes conditions relating to adverse reaction to food, which can be of non-allergic as well as allergic nature. Allergic food hypersensitivities can be IgE-mediated and are referred to as food allergies. Severe, generalized allergic reactions to food can involve anaphylaxis. In some embodiments of the invention, food hypersensitivity can include food allergies, preferably an IgE-mediated food allergy.

As used herein, the term "drug hypersensitivity" relates to hypersensitive reactions of the body towards drugs which can be of non-allergic as well as of allergic nature. When immunologic mechanisms have been shown, either antibody or cell mediated, the reactions are referred to as drug allergy. Drug allergies can be mediated by IgE. In some embodiments of the invention, drug hypersensitivity, encompasses drug allergies, for example, IgE-mediated drug allergies.

As used herein, the terms "insect sting hypersensitivity" or "insect bite hypersensitivity" relate to hypersensitive reactions towards insect venom and saliva which can be of non-allergic as well as allergic nature. Insect sting hypersensitivity or insect bite hypersensitivity mediated by an immunologic mechanism is referred to as venom or saliva allergy, as in bee venom allergy. The large quantity of venom allergen in a sting is comparable with years of inhaled pollen allergen. This high-dose sensitization probably explains why there is no need for a genetic predisposition for developing such an allergy. In some embodiments of the invention, "insect sting hypersensitivity" or "insect bite hypersensitivity" relate to venom allergy, for example, IgE-mediated venom allergy, including, but not limited to, IgE mediated insect (e.g. bees, wasps, mosquitoes, and ants) venom allergy.

As used herein, the term "anaphylaxis" refers to a severe, life-threatening, generalized or systemic hypersensitive reaction. The reaction usually develops gradually, most often starting with itching of the gums/throat, the palms, or the soles, and local urticaria; developing to a multiple organ reaction often dominated by severe asthma; and culminating in hypotension and shock. Hypotension and severe bronchospasm do not have to be present for a reaction to be classified as anaphylaxis. Anaphylaxis can be of non-allergic as well as of allergic nature. Allergic anaphylaxis involves an immunologic mechanism like an IgG immune complex, complement related, or immune cell-mediated mechanism. Anaphylaxis preferably relates to an anaphylactic reaction mediated by IgE antibodies (IgE-mediated anaphylaxis), most preferably to peanut-induced food anaphylaxis or bee venom-induced anaphylaxis.

As used herein, the term "allergen" refers to a substance causing allergy. Preferred allergens are allergens disclosed in Shough, H. et al., REMINGTON'S PHARMACEUTICAL SCIENCES, 19th edition, (Chap. 82), Mack Publishing Company, Mack Publishing Group, Easton, Pa. (1995), the entire contents of which is hereby incorporated by reference. Allergens serve as antigens in vertebrate animals. The term "allergen", as used herein, also refers to "allergen extracts" and "allergenic epitopes." In some embodiments, allergens include: pollens (e.g. grass, ragweed, birch and mountain cedar); house dust and dust mites; mammalian epidermal allergens and animal danders; mold and fungus; insect bodies and insect venom; feathers; food; and drugs (e.g. penicillin).

As used herein, the term "allergy inducing solution" can include a solution containing a biological and/or a chemical agent capable of inducing an allergic reaction in a subject. Biological agents can include allergens, for example, pollens (e.g. grass, ragweed, birch and mountain cedar); house dust and dust mites; mammalian epidermal allergens and animal danders; mold and fungus; insect bodies and insect venom; feathers and the like, generally, from a living organism. Chemical agents can include food allergens; and drugs (e.g. iodine, silver nitrate, MSG, preservatives, or antibiotics). In some embodiments, allergy inducing solutions can contain mixtures of different grasses, preferably of orchard grass, velvet grass, rye grass, timothy grass, Kentucky blue grass and/or Meadow fescue for example, mixtures of grasses, cereals, different trees and/or animal hair. Allergy inducing solutions can be prepared in physiological saline and can be preserved by addition of 0.1%-1.0% phenol or thimerosal.

As used herein, the term "allergen extracts" includes components of used for conjunctival, nasal and bronchial challenges. Such allergen extracts are commercially available and methods for producing such extracts are well-known. In some embodiments, single allergen extracts can be used to induce an allergic reaction when implanted, injected, contacted or otherwise exposed to a test subject. In some embodiments, the allergen extracts are provided in an allergy inducing solution comprising a single allergen extract which can be prepared from, for example, tree species or a grass species, most preferably selected from the group consisting of alder, ash, birch, hazel, orchard grass, velvet grass, rye grass, timothy grass, Kentucky blue grass, Meadow fescue, Bermuda grass, ragweed, rye and wheat; epithelia of different animal species, preferably epithelia from an animal species selected from the group consisting of cat, dog and horse; molds, exemplary molds can include: *Aspergillus* sp., *Candida* sp., *Alternaria* Sp., and *Saccharomyces* Sp.; and mite species, including, but not limited to: *Dermatophagoides farinae, Dermatophagoides pteronyssinus* and *Acarus siro*. Allergen extracts comprising allergen mixtures can also be used in allergy inducing solutions.

As used herein, "antibody": As used herein, the term "antibody" refers to molecules belonging to the class of immunoglobulins which are capable of binding an epitope or antigenic determinant.

As used herein, the term "antigen" refers to a molecule capable of being bound by an antibody or a T-cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. Antigens as used herein may also be mixtures of several individual antigens.

As used herein, the term "epitope" refers to continuous or discontinuous portions of a polypeptide having antigenic or immunogenic activity in an animal, preferably a mammal, and most preferably in a human.

As used herein, "Compound A," which is a compound of Formula I and of Table I, i.e. 4-[1-(5-methyl-pyridin-3-ylmethyl)-piperidin-4-ylidene]-4,9-dihydro-1-thia-benzo[f]azulen-10-one, means the structure:

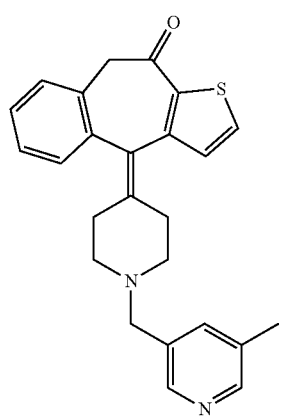

Compound A

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in Remington's Pharmaceutical Sciences, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent molecule is replaced by a metal ion, such as sodium, potassium, lithium, ammonium, calcium, magnesium, iron, zinc, copper, manganese, aluminum salts and the like. Specific salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the active ingredient of the above formulae, for example, by hydrolysis in blood. Common examples of a prodrug include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons).

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

Compounds

The present invention relates to compounds useful as inhibitors of allergic reactions. Compounds of the present invention are described by the following chemical Formula I:

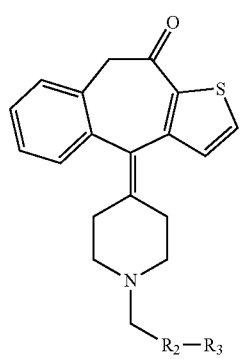

Formula I or a pharmaceutically acceptable salt, solvate or prodrug thereof, wherein $R_2$ is each independently $C_{1-8}$ alkyl, $C_{2-8}$ alkenyl, $C_{2-8}$ alkynyl, alkoxy, alkenoxy, $C_{4-10}$ cycloalkyl, $C_{4-10}$ heterocycloalkyl, $C_{4-10}$ aryl, $C_{4-10}$ aralkyl, aralkyloxy, $C_{4-10}$ heteroaryl, or $C_{4-10}$ heteroaralkyl, wherein each $C_{1-8}$ alkyl, $C_{2-8}$ alkenyl, $C_{2-8}$ alkynyl, alkoxy, alkenoxy, $C_{4-10}$ cycloalkyl, $C_{4-10}$ heterocycloalkyl, $C_{4-10}$ aryl, $C_{4-10}$ aralkyl, aralkyloxy, $C_{4-10}$ heteroaryl, or $C_{4-10}$ heteroaralkyl optionally including 1-3 substituents independently selected from $Q_1$ or $Q_2$;

$R_3$ is each independently, hydrogen, halo, OH, —ON, —$NO_2$, —N=O, —$NHOQ_1$, —$OQ_1$, —$SOQ_1$, —$SO_2Q_1$, —$SON(Q_1)_2$, —$SO_2N(Q_1)_2$, —$N(Q_1)_2$, —$C(O)OQ_1$, —$C(O)Q_1$, —$C(O)N(Q_1)_2$, —$C(=NQ_1)NQ_1$-, —$NQ_1C(=NQ_1)NQ_1$-, —$C(O)N(Q_1)(OQ_1)$, —$N(Q_1)C(O)$-$Q_1$, —$N(Q_1)C(O)N(Q_1)_2$, —$N(Q_1)C(O)O$-$Q_1$, —$N(Q_1)SO_2Q_1$, —$N(Q_1)SOQ_1$, $C_{1-8}$ alkyl, $C_{2-8}$ alkenyl, $C_{2-8}$ alkynyl, alkoxy, alkenoxy, $C_{4-10}$ cycloalkyl, $C_{4-10}$ heterocycloalkyl, $C_{4-10}$ aryl, $C_{4-10}$ aralkyl, aralkyloxy, $C_{4-10}$ heteroaryl, or $C_{4-10}$ heteroaralkyl, wherein each $C_{1-8}$ alkyl, $C_{2-8}$ alkenyl, $C_{2-8}$ alkynyl, alkoxy, alkenoxy, $C_{4-10}$ cycloalkyl, $C_{4-10}$ heterocycloalkyl, $C_{4-10}$ aryl, $C_{4-10}$ aralkyl, aralkyloxy, $C_{4-10}$ heteroaryl, or $C_{4-10}$ heteroaralkyl optionally substituted with 1-3 substituents independently selected from $Q_1$ or $Q_2$;

each $Q_1$ is independently hydrogen, $C_{1-8}$ alkyl, $C_{2-8}$ alkenyl, alkoxy, alkenoxy, $C_{4-10}$ cycloalkyl, $C_{4-10}$ aryl, $C_{4-10}$ arylalkyl, aralkyloxy, $C_{4-10}$ heterocyclic, or $C_{4-10}$ heteroaryl ring, each optionally including 1-3 substituents independently selected from $Q_2$;

each $Q_2$ is halo, haloalkyl, oxo, oxime, azido, amino, amido, cyano, CN, $NO_2$, $CF_3$, $OCF_3$, OH, —COOH or $C_1$-$C_4$ alkyl optionally substituted with 1-3 of halo, oxo, oxime, —CN, —$NO_2$, —$CF_3$, —$OCF_3$, —OH, —SH, —$S(O)_3H$, —$NH_2$, or —COOH.

The $R_2$ Variable

In some embodiments, $R_2$ is each independently $C_{1-8}$ alkyl, $C_{2-8}$ alkenyl, $C_{2-8}$ alkynyl, alkoxy, alkenoxy, $C_{4-10}$ cycloalkyl, $C_{4-10}$ heterocycloalkyl, $C_{4-10}$ aryl, $C_{4-10}$ aralkyl, aralkyloxy, $C_{4-10}$ heteroaryl, or $C_{4-10}$ heteroaralkyl, wherein each $C_{1-8}$ alkyl, $C_{2-8}$ alkenyl, $C_{2-8}$ alkynyl, alkoxy, alkenoxy, $C_{4-10}$ cycloalkyl, $C_{4-10}$ heterocycloalkyl, $C_{4-10}$ aryl, $C_{4-10}$ aralkyl, aralkyloxy, $C_{4-10}$ heteroaryl, or $C_{4-10}$ heteroaralkyl optionally substituted with 1-3 substituents independently selected from hydrogen, $C_{1-8}$ alkyl, $C_{2-8}$ alkenyl, alkoxy, alkenoxy, $C_{4-10}$ cycloalkyl, $C_{4-10}$ heterocycloalkyl, $C_{4-10}$ aryl, $C_{4-10}$ arylalkyl, aralkyloxy, or $C_{4-10}$ heteroaryl, wherein each $C_{1-8}$ alkyl, $C_{2-8}$ alkenyl, alkoxy, alkenoxy, $C_{4-10}$ cycloalkyl, $C_{4-10}$ heterocycloalkyl, $C_{4-10}$ aryl, $C_{4-10}$ arylalkyl, aralkyloxy, or $C_{4-10}$ heteroaryl optionally including 1-3 substituents independently selected from halo, oxo, oxime, azido, amino, amido, cyano, CN, $NO_2$, $CF_3$, $OCF_3$, OH, —COOH or $C_1$-$C_4$ alkyl optionally substituted with 1-3 of halo, oxo, oxime, —CN, —$NO_2$, —$CF_3$, —$OCF_3$, —OH, —SH, —$S(O)_3H$, —$NH_2$, or —COOH. In another embodiment, $R_2$ is $C_{1-8}$ alkyl, $C_{2-8}$ alkenyl, $C_{4-10}$ cycloalkyl, $C_{4-10}$ heterocycloalkyl, $C_{4-10}$ aryl, or $C_{4-10}$ heteroaryl. In another embodiment, $R_2$ is $C_{4-10}$ cycloalkyl, $C_{4-10}$ heterocycloalkyl or $C_{4-10}$ heteroaryl. In some embodiments, $R_2$ is a $C_{4-10}$ heterocycloalkyl or $C_{4-10}$ heteroaryl. In some embodiments, $R_2$ is a $C_{4-10}$ heteroaryl.

In some embodiments, $R_2$ is each independently $C_{4-10}$ alkyl, $C_{4-10}$ alkenyl, $C_{4-10}$ alkynyl, alkoxy, alkenoxy, $C_{4-10}$ cycloalkyl, $C_{4-10}$ heterocycloalkyl, $C_{4-10}$ aryl, $C_{4-10}$aralkyl, aralkyloxy, $C_{4-10}$ heteroaryl, or $C_{4-10}$ heteroaralkyl, wherein each $C_{4-10}$ alkyl, $C_{4-10}$ alkenyl, $C_{4-10}$ alkynyl, alkoxy, alkenoxy, $C_{4-10}$ cycloalkyl, $C_{4-10}$ heterocycloalkyl, $C_{4-10}$ aryl, $C_{4-10}$ aralkyl, aralkyloxy, $C_{4-10}$ heteroaryl, or $C_{4-10}$ heteroaralkyl optionally substituted with 1-3 substituents independently selected from hydrogen, $C_{1-8}$ alkyl, $C_{2-8}$ alkenyl, alkoxy, alkenoxy, $C_{4-10}$ cycloalkyl, $C_{4-10}$ heterocycloalkyl, $C_{4-10}$ aryl, $C_{4-10}$ arylalkyl, aralkyloxy, or $C_{4-10}$ heteroaryl, wherein each $C_{1-8}$ alkyl, $C_{2-8}$ alkenyl, alkoxy, alkenoxy, $C_{4-10}$ cycloalkyl, $C_{4-10}$ heterocycloalkyl, $C_{4-10}$ aryl, $C_{4-10}$ arylalkyl, aralkyloxy, or $C_{4-10}$ heteroaryl optionally including 1-3 substituents independently selected from halo, oxo, oxime, azido, amino, amido, cyano, CN, $NO_2$, $CF_3$, $OCF_3$, OH, —COOH or $C_1$-$C_4$ alkyl optionally substituted with 1-3 of halo, oxo, oxime, —CN, —$NO_2$, —$CF_3$, —$OCF_3$, —OH, —SH, —$S(O)_3H$, —$NH_2$, or —COOH.

In another embodiment, $R_2$ is $C_{4-8}$ alkyl, $C_{4-8}$ alkenyl, $C_{4-10}$ cycloalkyl, $C_{4-10}$ heterocycloalkyl, $C_{4-10}$ aryl, or $C_{4-10}$ heteroaryl. In another embodiment, $R_2$ is $C_{4-10}$ cycloalkyl, $C_{4-10}$ heterocycloalkyl or $C_{4-10}$ heteroaryl. In some aspects, $R_2$ is a $C_{4-10}$ heterocycloalkyl or a $C_{4-10}$ heteroaryl. In some embodiments, $R_2$ is a $C_{4-10}$ heteroaryl. In some aspects, $R_2$ is piperidine, azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl. pyridine-N-oxide, 1-piperidinyl, 2-piperidinyl, 3-piperidinyl, 4-piperidinyl, N-methyl-piperidinyl, N-ethyl-piperidinyl, N-propyl-piperidinyl, hexahydrothiopyranyl, azepanyl, methylazepanyl, tetrahydropyranyl, piperidinylmethyl, pyridinyl, pyridinylmethyl, tetrahydrothiopyranyl, dioxolanylmethyl, dioxanylmethyl. N-isopropyl-piperidinyl, N-butyl-piperidinyl, N-pentyl-piperidinyl, N-hexylpiperidinyl, N-cyclohexyl-piperidinyl, N-acetyl-piperidinyl, N-benzyl-piperidinyl. In some embodiments, $R_2$ is pyridine.

In some embodiments, $R_2$ is selected from:

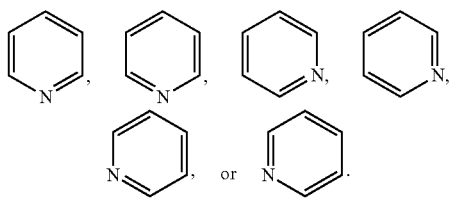

The $R_3$ Variable

In some embodiments, $R_3$ is each independently hydrogen, halo, OH, —CN, —$NO_2$, —N=O, —$NHOQ_1$, —$OQ_1$, —$SOQ_1$, —$SO_2Q_1$, —$SON(Q_1)_2$, —$SO_2N(Q_1)_2$, —$N(Q_1)_2$, —$C(O)OQ_1$, —$C(O)Q_1$, —$C(O)N(Q_1)_2$, —$C(=NQ_1)NQ_1$-, —NQ$_1$C(=NQ$_1$)NQ$_1$-, —C(O)N(Q$_1$)(OQ$_1$), —N(Q$_1$)C(O)-Q$_1$, —N(Q$_1$)C(O)N(Q$_1$)$_2$, —N(Q$_1$)C(O)O-Q$_1$, —N(Q$_1$)SO$_2$Q$_1$, —N(Q$_1$)SOQ$_1$, C$_{1-8}$ alkyl, C$_{2-8}$ alkenyl, C$_{2-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, C$_{4-10}$ heteroaralkyl, wherein each C$_{1-8}$ alkyl, C$_{2-8}$ alkenyl, C$_{2-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, C$_{4-10}$ heteroaralkyl optionally substituted with 1-3 substituents independently selected from halo, haloalkyl, oxo, oxime, azido, amino, amido, cyano, CN, NO$_2$, CF$_3$, OCF$_3$, OH, —COOH or C$_1$-C$_4$ alkyl optionally substituted with 1-3 of halo, oxo, oxime, —CN, —NO$_2$, —CF$_3$, —OCF$_3$, —OH, —SH, —S(O)$_3$H, —NH$_2$, or —COOH.

each Q$_1$ is independently hydrogen, C$_{1-8}$ alkyl, C$_{2-8}$ alkenyl, alkoxy, alkenoxy, C$_{4-10}$ cycloalkyl, C$_{4-10}$ aryl, C$_{4-10}$ arylalkyl, aralkyloxy, C$_{4-10}$ heterocyclic, or C$_{4-10}$ heteroaryl ring, each optionally including 1-3 substituents independently selected from Q$_2$;

each Q$_2$ is halo, haloalkyl, oxo, oxime, azido, amino, amido, cyano, CN, NO$_2$, CF$_3$, OCF$_3$, OH, —COOH or C$_1$-C$_4$ alkyl optionally substituted with 1-3 of halo, oxo, oxime, —CN, —NO$_2$, —CF$_3$, —OCF$_3$, —OH, —SH, —S(O)$_3$H, —NH$_2$, or —COOH. In some embodiments, R$_3$ is each independently selected from H, C$_{1-8}$ alkyl, C$_{2-8}$ alkenyl, C$_{2-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, or C$_{4-10}$ heteroaralkyl. In another embodiment, R$_3$ is H or C$_{1-8}$ alkyl. In some embodiments, R$_3$ is hydrogen, methyl, ethyl, propyl, isopropyl, butyl, isobutyl, hexyl, 2-ethylpropyl, or cyclohexyl. In some embodiments, R$_3$ is hydrogen or methyl.

In some embodiments, R$_3$ is each independently selected from H, C$_{1-8}$ alkyl, C$_{1-8}$ alkenyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, C$_{4-10}$ heteroaralkyl.

Formula Ia

The present invention relates to compounds useful as inhibitors of allergic reactions. Compounds of the present invention are described by the following chemical Formula Ia:

Formula Ia or a pharmaceutically acceptable salt, solvate or prodrug thereof, wherein In some embodiments, R$_3$ is each independently hydrogen, halo, OH, —CN, —NO$_2$, —N=O, —NHOQ$_1$, —OQ$_1$, —SOQ$_1$, —SO$_2$Q$_1$, —SON(Q$_1$)$_2$, —SO$_2$N(Q$_1$)$_2$, —N(Q$_1$)$_2$, —C(O)OQ$_1$, —C(O)Q$_1$, —C(O)N(Q$_1$)$_2$, —C(=NQ$_1$)NQ$_1$-, —NQ$_1$C(=NQ$_1$)NQ$_1$-, —C(O)N(Q$_1$)(OQ$_1$), —N(Q$_1$)C(O)-Q$_1$, —N(Q$_1$)C(O)N(Q$_1$)$_2$, —N(Q$_1$)C(O)O-Q$_1$, —N(Q$_1$)SO$_2$Q$_1$, —N(Q$_1$)SOQ$_1$, C$_{1-8}$ alkyl, C$_{2-8}$ alkenyl, C$_{2-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, C$_{4-10}$ heteroaralkyl, wherein each C$_{1-8}$ alkyl, C$_{2-8}$ alkenyl, C$_{2-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, C$_{4-10}$ heteroaralkyl optionally substituted with 1-3 substituents independently selected from halo, haloalkyl, oxo, oxime, azido, amino, amido, cyano, CN, NO$_2$, CF$_3$, OCF$_3$, OH, —COOH or C$_1$-C$_4$ alkyl optionally substituted with 1-3 of halo, oxo, oxime, —CN, —NO$_2$, —CF$_3$, —OCF$_3$, —OH, —SH, —S(O)$_3$H, —NH$_2$, or —COOH.

each Q$_1$ is independently hydrogen, C$_{1-8}$ alkyl, C$_{2-8}$ alkenyl, alkoxy, alkenoxy, C$_{4-10}$ cycloalkyl, C$_{4-10}$ aryl, C$_{4-10}$ arylalkyl, aralkyloxy, C$_{4-10}$ heterocyclic, or C$_{4-10}$ heteroaryl ring, each optionally including 1-3 substituents independently selected from Q$_2$;

each Q$_2$ is halo, haloalkyl, oxo, oxime, azido, amino, amido, cyano, CN, NO$_2$, CF$_3$, OCF$_3$, OH, —COOH or C$_1$-C$_4$ alkyl optionally substituted with 1-3 of halo, oxo, oxime, —CN, —NO$_2$, —CF$_3$, —OCF$_3$, —OH, —SH, —S(O)$_3$H, —NH$_2$, or —COOH. In some embodiments, R$_3$ is each independently selected from H, C$_{1-8}$ alkyl, C$_{2-8}$ alkenyl, C$_{2-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, or C$_{4-10}$ heteroaralkyl. In another embodiment, R$_3$ is H or C$_{1-8}$ alkyl. In some embodiments, R$_3$ is hydrogen, methyl, ethyl, propyl, isopropyl, butyl, isobutyl, hexyl, 2-ethylpropyl, or cyclohexyl. In some embodiments, R$_3$ is hydrogen or methyl.

TABLE 1

Exemplary Compounds Of Formula I

| Compound Number | Structure and Formula |
|---|---|
| 1 | 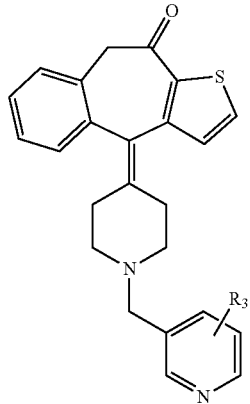<br>C$_{24}$H$_{22}$N$_2$OS<br>4-(1-Pyridin-3-ylmethyl-piperidin-4-ylidene)-4,9-dihydro-1-thia-benzo[f]azulen-10-one |

TABLE 1-continued

Exemplary Compounds Of Formula I

| Compound Number | Structure and Formula |
|---|---|
| 2 | 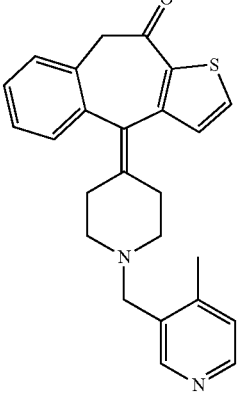 $C_{25}H_{24}N_2OS$<br>4-[1-(4-Methyl-pyridin-3-ylmethyl)-piperidin-4-ylidene]-4,9-dihydro-1-thia-benzo[f]azulen-10-one |
| 3 | 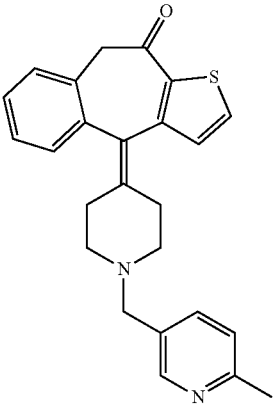 [SMILES: Cc1ccc(CN2CCC(=C3c4ccccc4CC(=O)c4sccc43)CC2)cn1] $C_{25}H_{24}N_2OS$<br>4-[1-(6-Methyl-pyridin-3-ylmethyl)-piperidin-4-ylidene]-4,9-dihydro-1-thia-benzo[f]azulen-10-one |
| 4 | 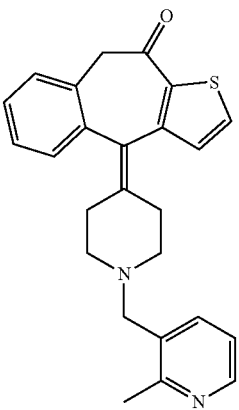 [SMILES: Cc1ncccc1CN1CCC(=C2c3ccccc3CC(=O)c3sccc32)CC1] $C_{25}H_{24}N_2OS$<br>4-[1-(2-Methyl-pyridin-3-ylmethyl)-piperidin-4-ylidene]-4,9-dihydro-1-thia-benzo[f]azulen-10-one |
| 5 | 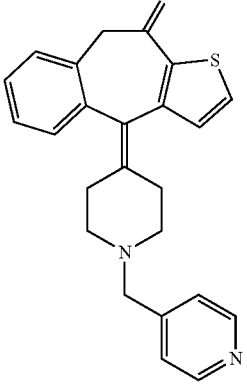 $C_{24}H_{22}N_2OS$<br>4-(1-Pyridin-4-ylmethyl-piperidin-4-ylidene)-4,9-dihydro-1-thia-benzo[f]azulen-10-one |
| 6 | 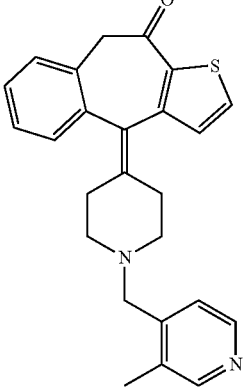 $C_{25}H_{24}N_2OS$<br>4-[1-(3-Methyl-pyridin-4-ylmethyl)-piperidin-4-ylidene]-4,9-dihydro-1-thia-benzo[f]azulen-10-one |
| 7 | 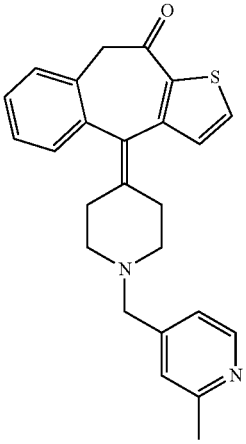 [SMILES: Cc1cc(CN2CCC(=C3c4ccccc4CC(=O)c4sccc43)CC2)ccn1] $C_{25}H_{24}N_2OS$<br>4-[1-(2-Methyl-pyridin-4-ylmethyl)-piperidin-4-ylidene]-4,9-dihydro-1-thia-benzo[f]azulen-10-one |

TABLE 1-continued

Exemplary Compounds Of Formula I

| Compound Number | Structure and Formula |
|---|---|
| 8 | 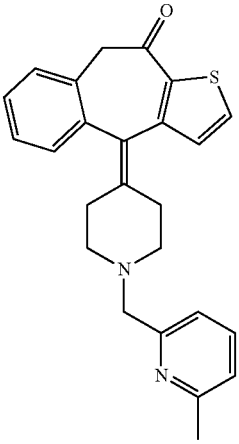 [SMILES: Cc1cccc(CN2CCC(=C3c4ccccc4CC(=O)c4sccc43)CC2)n1]<br>$C_{25}H_{24}N_2OS$<br>4-[1-(6-Methyl-pyridin-2-ylmethyl)-piperidin-4-ylidene]-4,9-dihydro-1-thia-benzo[f]azulen-10-one |
| 9 | 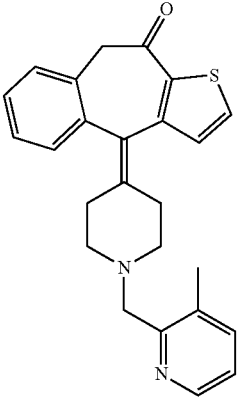 [SMILES: Cc1cccnc1CN1CCC(=C2c3ccccc3CC(=O)c3sccc32)CC1]<br>$C_{25}H_{24}N_2OS$<br>4-[1-(3-Methyl-pyridin-2-ylmethyl)-piperidin-4-ylidene]-4,9-dihydro-1-thia-benzo[f]azulen-10-one |
| 10 | 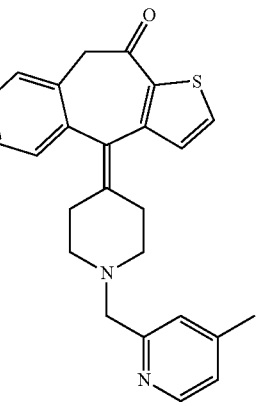<br>$C_{25}H_{24}N_2OS$<br>4-[1-(4-Methyl-pyridin-2-ylmethyl)-piperidin-4-ylidene]-4,9-dihydro-1-thia-benzo[f]azulen-10-one |
| 11 | 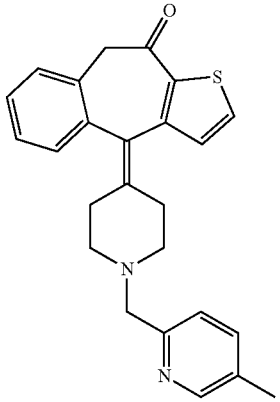 [SMILES: Cc1ccc(CN2CCC(=C3c4ccccc4CC(=O)c4sccc43)CC2)nc1]<br>$C_{25}H_{24}N_2OS$<br>4-[1-(5-Methyl-pyridin-2-ylmethyl)-piperidin-4-ylidene]-4,9-dihydro-1-thia-benzo[f]azulen-10-one |
| 12 | 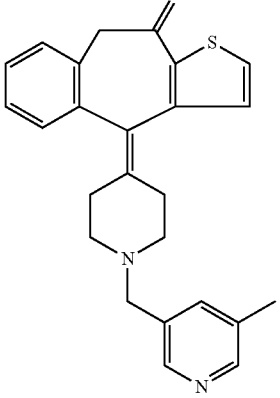<br>Molecular Formula = $C_{25}H_{24}N_2OS$<br>4-[1-(5-Methyl-pyridin-3-ylmethyl)-piperidin-4-ylidene]-4,9-dihydro-1-thia-benzo[f]azulen-10-one |

In some embodiments, the present invention also includes pharmaceutically acceptable addition salts of the compounds of Formula I. The compounds of the present invention can be added to organic and inorganic acids to form these pharmaceutically acceptable addition salts. Pharmaceutically acceptable addition salts of compounds of Formula I are also part of the present invention. There is no limitation on the nature of these salts, provided that, when used for therapeutic purposes, they are pharmaceutically acceptable, which, as is well known in the art. For example, pharmaceutically acceptable salts can include salts that are pharmaceutically acceptable acid addition salts. Examples of these salts include: salts with an inorganic acid such as hydrochloric acid, hydrobromic acid, hydriodic acid, nitric acid, perchloric acid, sulfuric acid or phosphoric acid; and salts with an organic acid, such as methanesulfonic acid, trifluoromethanesulfonic acid, ethanesulfonic acid, benzenesulfonic acid, p-toluenesulfonic acid, fumaric acid, oxalic acid, maleic acid, citric acid; and other mineral and carboxylic acids well known to those skilled in the art. The salts are prepared by contacting the free base form with a sufficient amount of the desired acid to produce a salt in the conventional manner. The free base form differs from its salt forms somewhat in certain physical properties, such as solubility in polar solvents, but they are equivalent for purposes of the invention.

In some embodiments, the compound of Formula I can exist in unsolvated as well as solvated forms, including hydrated forms. In general, the solvated forms, with pharmaceutically acceptable solvents such as water, ethanol and the like are equivalent to the unsolvated form for purposes of the invention.

Compositions

In another embodiment, this invention provides pharmaceutical compositions comprising the above-described inventive compounds of Formula I as an active ingredient. The pharmaceutical compositions generally additionally comprise a pharmaceutically acceptable vehicle, diluent, excipient or carrier (collectively referred to herein as excipient materials or non-active ingredient). The pharmaceutical compositions of the present invention possess utility in treating allergic diseases and conditions, inflammation, ocular irritation, "dry eye" conditions (xeropthalmia), nasal congestion, respiratory airway inflammation diseases such as asthma and the like diseases.

In some embodiments, the present invention discloses methods for preparing pharmaceutical compositions comprising the inventive compounds of Formula I as an active ingredient. In the pharmaceutical compositions and methods of the present invention, the active ingredient will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, sprays, liquid drops, washes, ointments, topical liposome formulations and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. antihistaminic activity and the like. Suitable dosage forms for sustained release include layered tablets containing layers of varying disintegration rates or polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Also included are solid form preparations which are intended to be converted, shortly before use, to liquid form preparations for either oral or parenteral administration. Such liquid forms include solutions, suspensions and emulsions.

The compounds of Formula I may also be deliverable transdermally. The transdermal compositions may take the form of creams, lotions, aerosols and/or emulsions and can be included in a transdermal patch of the matrix or reservoir type as are conventional in the art for this purpose.

The choice of formulation depends on various factors such as the mode of drug administration (e.g., for oral administration, formulations in the form of tablets, pills or capsules) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the compound of Formula I is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the compound or compounds of Formula I in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of Formula I, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. In some embodiments, the compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of Formula I include ointments, powders, sprays, and inhalants. The active component is admixed under sterile conditions with a physiologically acceptable carrier and any preservatives, buffers, or propellants as may be required. Compressed gases may be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the present invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being one or more suitable pharmaceutical excipients. If formulated as a fixed dose, such products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

Preferably, the pharmaceutical preparation is in a unit dosage form. In such form, the preparation is subdivided into suitably sized unit doses containing appropriate quantities of the active components, e.g., a therapeutically effective amount of a compound of Formula I to achieve the desired purpose. In some embodiments, a pharmaceutical composition comprises a quantity of the inventive compound of Formula I formulated in a unit dose form which may be generally varied or adjusted from about 0.01 milligram to about 100 milligrams, preferably from about 0.1 to about 50 milligrams, more preferably from about 0.5 to about 25 milligrams, and typically from about 1 to about 10 milligrams, according to the particular application. In some embodiments, a pharmaceutical composition comprises a therapeutically effective amount of a selective anti-allergy benzocycloheptathiophene derivative compound of Formula I, or a compound of Formula I, or a compound as recited in Table 1, and a pharmaceutically acceptable carrier, vehicle or excipient. In some embodiments, the present invention provides a pharmaceutical composition comprising a therapeutically effective amount of a selective anti-allergy benzocycloheptathiophene derivative compound, wherein the selective anti-allergy benzocycloheptathiophene derivative compound is recited in Table 1, and the compound is in admixture with a pharmaceutically acceptable carrier, vehicle or excipient. Another illustrative pharmaceutical composition can include a therapeutically effective amount of a selective anti-allergy benzocycloheptathiophene derivative compound comprising 4-[1-(5-methyl-pyridin-3-ylmethyl)-piperidin-4-ylidene]-4,9-dihydro-1-thia-benzo[f]azulen-10-one, in admixture with a pharmaceutically acceptable carrier, vehicle or excipient. In one example of a pharmaceutical composition, the pharmaceutical composition comprises a pharmaceutical unit-dose composition comprising a selective anti-allergy benzocycloheptathiophene derivative compound of Formula I, the compound is present in the pharmaceutical unit-dose composition in an amount ranging from about 0.01 milligram to about 100 milligrams, preferably from about 0.1 to about 50 milligrams, more preferably from about 0.5 to about 25 milligrams, and typically from about 1 to about 10 milligrams, the compound is in admixture with at least one pharmaceutically acceptable carrier, vehicle or excipient. Still further examples of pharmaceutical compositions include a pharmaceutical unit-dose composition comprising a selective anti-allergy benzocycloheptathiophene derivative compound provided in Table 1, the compound is present in the pharmaceutical unit-dose composition in an amount ranging from about 0.01 milligram to about 100 milligrams, preferably from about 0.1 to about 50 milligrams, more preferably from about 0.5 to about 25 milligrams, and typically from about 1 to about 10 milligrams, the compound is in admixture with at least one pharmaceutically acceptable carrier, vehicle or excipient. In some embodiments, the pharmaceutical unit-dose composition comprises a therapeutically effective amount of 4-[1-(5-methyl-pyridin-3-ylmethyl)-piperidin-4-ylidene]-4,9-dihydro-1-thia-benzo[f]azulen-10-one, the compound is present in the pharmaceutical unit-dose composition in an amount ranging from about 0.01 milligram to about 100 milligrams, preferably from about 0.1 to about 50 milligrams, more preferably from about 0.5 to about 25 milligrams, and typically from about 1 to about 10 milligrams, the compound is in admixture with at least one pharmaceutically acceptable carrier, vehicle or excipient.

The actual dosage employed may be varied depending upon the patient's age, sex, weight and severity of the condition being treated. Such techniques are well known to those skilled in the art. In one illustrative embodiment, a unit dose comprises a solid tablet pharmaceutical composition containing 1 mg of Compound A in the free base form, equivalent to about 1.29 mg Compound A in the hydrogen fumarate salt form. In another illustrative embodiment, 5 mL of a syrup is a unit dose containing 1 mg/5 mL of Compound A in free base form which is equivalent to 1.29 mg/5 mL Compound A in the hydrogen fumarate salt form.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a Compound of the invention, or a pharmaceutically acceptable salt thereof, for treatment of a disease-state in accordance with the teachings of this invention.

Ophthalmic Compositions

Ophthalmic formulations including eye ointments, powders, sprays, liquid drops, washes, ointments, topical liposome formulations are also contemplated as being within the scope of this invention. As used herein, "concentration" of a component of an ophthalmic composition means concentration based on mass of the component per total volume of the composition (i.e., g/mL, or wt/vol), and is typically expressed as a percentage.

In some embodiments, an ophthalmic composition can include a concentration of a compound of formula I, in a free base form, or an equivalent salt form, for example, a fumarate salt form, ranging from about 0.01% to about 0.1%, or from about 0.02% to about 0.05% in admixture with a suitable ophthalmic carrier. In some embodiments, an ophthalmic composition can include a concentration of 4-[1-(5-methyl-pyridin-3-ylmethyl)-piperidin-4-ylidene]-4,9-dihydro-1-thia-benzo[f]azulen-10-one ranging from about 0.01% to about 0.1% (wt/vol). In some embodiments, for topical ophthalmic administration, the ophthalmic carrier can include: water, mixtures of water and water-miscible solvents, such as $C_1$- to $C_7$-alkanols, vegetable oils or mineral oils comprising from 0.5 to 5 percent by weight ethyl oleate, hydroxyethylcellulose, carboxymethylcellulose, polyvinylpyrrolidone and other non-toxic water-soluble polymers for ophthalmic uses, may include, cellulose derivatives, such as methylcellulose, alkali metal salts of carboxymethylcellulose, hydroxymethylcellulose, hydroxyethylcellulose, methylhydroxypropylcellulose and hydroxypropylcellulose, acrylates or methacrylates, such as salts of polyacrylic acid or ethyl acrylate, polyacrylamides, natural products, such as gelatin, alginates, pectins, tragacanth, karaya gum, xanthan gum, carrageenan, agar and acacia, starch derivatives, such as starch acetate and hydroxypropyl starch, and also other synthetic products, such as polyvinyl alcohol, polyvinyl pyrrolidone, polyvinyl methyl ether, polyethylene oxide, preferably cross-linked polyacrylic acid, such as neutral Carbopol, or mixtures of those polymers. Preferred carriers are water, cellulose derivatives, such as methylcellulose, salts of carboxymethylcellulose, hydroxymethylcellulose, hydroxyethylcellulose, methylhydroxypropylcellulose and hydroxypropylcellulose, neutral Carbopol, or mixtures thereof. A highly preferred carrier is water. The concentration of the carrier is, for example, from 1 to 100,000 times the concentration of the active ingredient.

In some embodiments, the ophthalmic composition for topical administration may optionally also include a non-ionic tonicity agent. In some embodiments, a non-ionic tonicity agent includes glycerol, although other non-ionic tonicity agents may be used such as, for example, urea, sorbitol, mannitol, propylene glycol, and dextrose. In some embodiments, the non-ionic tonicity agent is provided in a concentration such that the composition has an osmolality from 400 to 750 milliosmoles/kilogram (mOsm/Kg), preferably from 425 to 700 mOsm/Kg, more preferably from 550 to 700 mOsm/Kg, even more preferably from 600 to 700 mOsm/Kg, and yet even more preferably from 650 to 700 mOsm/Kg. In some embodiments, glycerol is used as the non-ionic tonicity agent in a concentration of from 3% to 10%, preferably from 4% to 8%, more preferably from 5% to 7%, even more preferably from 5.5. % to 6.5%, and yet even more preferably from 5.75% to 6.25%. In yet other embodiments, glycerol is used as the non-ionic tonicity agent in a concentration of greater than 3.5%, preferably greater than 4.5%, more preferably greater than 5.5%, even more preferably from 5% to 7%, and yet even more preferably from 5.5% to 6.5%, such that the composition has an osmolality from 400 to 750 mOsm/Kg, preferably from 425 to 700 mOsm/Kg, more preferably from 550 to 700 mOsm/Kg, even more preferably from 600 to 700 mOsm/Kg, and yet even more preferably from 650 to 700 mOsm/Kg.

The ophthalmic compositions of the present invention may optionally also include one or more preservatives, particularly when the composition is packaged as a multi-dose application. Illustrative preservatives can include: benzalkonium chloride, polyquad preservative (Alcon); perborate (e.g., sodium perborate from Ciba); purite preservative (stabilized chlorine dioxide) (Allergan); other quaternary ammonium compounds such as benzoxonium chloride; alkyl-mercury salts of thiosalicylic acid such as, for example, thiomersal, phenylmercuric nitrate, phenylmercuric acetate, and phenylmercuric borate; parabens such as, for example, methylparaben or propylparaben; alcohols such as, for example, chlorobutanol, benzyl alcohol, and phenyl ethanol; guanidine derivatives such as, for example, chlorhexidine or polyhexamethylene biguanide; and the like. When a preservative is used in the ophthalmic composition, the preservative is typically provided in a concentration of 0.005% to 0.02%, preferably 0.01%, although other concentrations may be used.

In one embodiment, a solution to be used as an eyedrop liquid suspension comprises about 0.025% of Compound A in free base form which is equivalent to Compound A in hydrogen fumarate salt form at 0.032%.

In one illustrative example, an ophthalmic composition in the form of a topical solution can include: (1) Compound A, 0.25 mg (0.025%); (2) Benzalkonium chloride, 0.10 mg (0.010%); (3) Glycerol 100%, 21.25 mg (2.125%); (4) Sodium hydroxide 1 N, about 0.75 mg (.about. 0.075%); and (5) Water for injection (sterile) to make up 1.0 mL.

Methods of Administering

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular, intraperitoneal or intravenous injection. Typically, dosages of the compound of the invention which may be administered to an animal, preferably a human, will vary depending upon any number of factors, including but not limited to, the type of animal and type of disease state being treated, the age of the animal and the route of administration.

Pharmaceutical compositions of the invention formulated for pulmonary delivery may also provide the active ingredient or active ingredients, in the form of droplets of a solution or suspension. Such formulations may be prepared, packaged, or sold as aqueous or dilute alcoholic solutions or suspensions, optionally sterile, comprising the active ingredient, or active ingredients and may conveniently be administered using any nebulization or atomization device. Such formulations may further comprise one or more additional non-active ingredients for example, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers. The formulations described herein as being useful for pulmonary delivery are also useful for intranasal delivery of a pharmaceutical composition of the invention.

In some embodiments, an exemplary formulation suitable for intranasal administration is a coarse powder comprising the active ingredient and having an average particle size or diameter from about 0.2 to 500 micrometers. Such a formulation can be administered by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 50% (w/w) active ingredient, (and ranges inherent therein) the balance comprising an orally dissolvable or degradable composition and, optionally, one or more of the additional non-active ingredients described herein. Alternately, formulations suitable for buccal administration may comprise a powder or an aerosolized or atomized solution or suspension comprising the active ingredient or active ingredients. Such powdered, aerosolized, or aerosolized formulations, when dispersed, preferably have an average particle or droplet size in the range from about 0.1 to about 200 nanometers, and may further comprise one or more of the additional non-active ingredients described herein.

As used herein, "additional non-active ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional non-active ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. Generally, the human oral dosage form containing the active ingredients can be administered 1 or 2 times per day. The amount and frequency of the administration will be regulated according to the judgment of the attending clinician. The compounds of the present invention can be administered to a patient at dosage levels in the range of about 0.01 to about 100 mg per day in single or divided doses. For a normal human adult having a body weight of about 70 kilograms, a dosage in the range of about 0.0001 to about 10 mg per kilogram of body weight per day, or more preferably from about 0.0005 to about 1 mg per kilogram of body weight per day, or from about 0.001 to about 0.5 mg per kilogram of body weight is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

For ophthalmic compositions, typically, the compositions are administered as drops, with one drop of the composition being applied to an eye of the subject suffering from or susceptible to allergic conjunctivitis two times per day, although more or less of the composition may be used in more or less frequent doses depending on multiple factors, including the makeup of the particular composition.

Typically, in therapeutic applications, the treatment would be for the duration of the disease state or condition. Further, it will be apparent to one of ordinary skill in the art that the optimal quantity and spacing of individual dosages will be determined by the nature and extent of the disease state or condition being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests. The administration of the pharmaceutical compositions above can be repeated several times, preferably at least one to five times, in daily, weekly, or monthly intervals. In some embodiments, a unit dose may be administered one to three times per day or once per day in sustained release form, to relieve one or more symptoms of allergy or allergic diseases described herein. The frequency of dosing can be experimentally verified in clinical trials and are recommended to provide a reasonable benefit/risk ratio commensurate with the experience of the prescribing clinician. Methods for determining the therapeutic effectiveness of the compositions described herein for the treatment of various allergic diseases or conditions are well within the skill of the ordinary artisan. For example, symptoms of atopic dermatitis can, for example be scored as described in N. Engl. J. Med 1997, 337:816-21. Symptoms of asthma can be scored by various methods including questionnaires described in Juniper et al., Health Qual. Life Outcomes, 2005 Sep. 16, 3:58, and combinations of questionnaires and spirometric measurements, for example, the severity of asthma symptoms can be assessed by spirometric measurements of pulmonary functions before and after administration of methacholine as described in N. Engl. J. Med 2000, 343:1054-63. These references are incorporated herein by reference. Pollen allergy can, inter alia, be assessed using a nasal provocation test, other allergies, e.g. food allergens, chemical allergens, plant allergens, house dust or dust mite allergens, can be assessed using a conjunctival provocation procedure or a skin prick test routinely used in immunology or allergy clinics.

Methods of Treating Allergic Diseases and Disorders

In some embodiments, the present invention provides methods for treating an allergic disease or symptoms associated therewith in a subject in need thereof, the method comprising administering a therapeutically effective amount of an anti-allergy benzocycloheptathiophene derivative compound of Formula I or a pharmaceutically acceptable salt thereof, solvate, or prodrug thereof, and a pharmaceutically acceptable carrier, vehicle or excipient. In some embodiments, the compound of Formula I is in the form of a fumarate salt. In some embodiments, the fumarate salt of the compound of Formula I is a fumarate salt of a compound of Table 1. In some embodiments, the fumarate salt of the compound of Formula I is a fumarate salt of 4-[1-(5-methyl-pyridin-3-ylmethyl)-piperidin-4-ylidene]-4,9-dihydro-1-thia-benzo[f]azulen-10-one. In some embodiments, the compound of Formula I can be in admixture with one or more pharmaceutically acceptable excipients (non-active ingredients) as described above. Optionally, the pharmaceutical composition may contain one or more additional therapeutic agents as described below for the treatment of an allergy, allergic disease, hypersensitive associated disease or respiratory disease associated with airway inflammation, such as asthma. In some embodiments, the compositions of the present invention are effective in preventing, treating or alleviating one or more symptoms related to anaphylaxis, drug hypersensitivity, skin allergy, eczema, allergic rhinitis, urticaria, atopic dermatitis, dry eye disease, allergic contact allergy, food hypersensitivity, allergic conjunctivitis, insect venom allergy, bronchial asthma, allergic asthma, intrinsic asthma, occupational asthma, atopic asthma, acute respiratory distress syndrome (ARDS) and chronic obstructive pulmonary disease (COPD).

Hypersensitivity associated diseases or disorders that may be treated by the methods of the invention include, but are not limited to, anaphylaxis, drug reactions, skin allergy, eczema, allergic rhinitis, urticaria, atopic dermatitis, dry eye disease (or otherwise referred to as Keratoconjunctivitis sicca (KCS), also called keratitis sicca, xerophthalmia), allergic contact allergy, food allergy, allergic conjunctivitis, insect venom allergy and respiratory diseases associated with airway inflammation, for example, IgE mediated asthma and non-IgE mediated asthma.

The respiratory diseases associated with airway inflammation may include, but are not limited to, rhinitis, allergic rhinitis, bronchial asthma, allergic (extrinsic) asthma, non-allergic (intrinsic) asthma, occupational asthma, atopic asthma, exercise induced asthma, cough-induced asthma, acute respiratory distress syndrome (ARDS) and chronic obstructive pulmonary disease (COPD). In some embodiments, the present invention provides methods for treating or alleviating the symptoms of an allergic disease, the method comprises administering a therapeutically effective amount of an anti-allergy benzocycloheptathiophene derivative compound of Formula I or a pharmaceutically acceptable salt thereof, solvate, or prodrug thereof, and a pharmaceutically acceptable carrier, vehicle or excipient to the subject. In some embodiments, the present invention provides a method for treating asthma in a subject in need thereof, the method comprises administering a therapeutically effective amount of an anti-allergy benzocycloheptathiophene derivative compound of Formula I or a pharmaceutically acceptable salt thereof, solvate, or prodrug thereof. In some embodiments, the compound of Formula I, can be present in a composition in a free base form, or an equivalent salt form, for example, a fumarate salt form, in a unit dose or a daily dose ranging from about 0.0001 to about 10 mg per kilogram of body weight, or from about 0.0005 to about 1 mg per kilogram of body weight. In some embodiments, the compound of Formula I can be present in a composition in a free base form, or an equivalent salt form, in admixture with a suitable pharmaceutical carrier, vehicle or excipient. In some embodiments, a method for treating asthma in a subject in need thereof comprises administering a composition containing 4-[1-(5-methyl-pyridin-3-ylmethyl)-piperidin-4-ylidene]-4,9-dihydro-1-thia-benzo[f]azulen-10-one or a pharmaceutically acceptable salt thereof, or solvate or prodrug thereof, the 4-[1-(5-methyl-pyridin-3-ylmethyl)-piperidin-4-ylidene]-4,9-dihydro-1-thia-benzo[f]azulen-10-one is administered in a unit dose or a daily dose ranging from about 0.0001 to about 10 mg per kilogram of body weight, or from about 0.0005 to about 1 mg per kilogram of body weight. In some embodiments, a method for treating asthma comprises administering a therapeutically effective amount of an anti-allergy benzocycloheptathiophene derivative compound of Formula I or Table 1, or a pharmaceutically acceptable salt thereof, solvate, or prodrug thereof, wherein the compound or pharmaceutically acceptable salt thereof, solvate, or prodrug thereof is administered to the subject in an amount from 0.0001 to about 10 mg per kilogram of body weight per day.

In one embodiment, the invention provides compositions comprising a compound of Formula I and methods for treating pulmonary diseases by way of oral or inhalation administration of the compositions of the invention. Preferably, the composition prevents hyper-responsiveness in airway and reduces the hypersensitivity of the airway due to mast cell involvement (for example, IgE mediated mast cell degranulation) and cytokine overproduction by immune effector cells such as mast cells, basophils, eosinophils, neutrophils, monocytes, macrophages, dendritic cells and T-cells. In one aspect, the compositions of the invention prevent bronchoconstriction in response to histamine and cholinergic challenges. In another aspect, the compositions diminish IL-13-induced hyper responsiveness to cholinergics. In yet another aspect, the compositions block bronchoconstriction secondary to IgE-mediated mast cell degranulation and improper cytokine immune responses.

In some embodiments, the compound of Formula I and/or an additional therapeutic agent described in detail below can be administered in therapeutically effective doses, or alternatively in subclinical effective doses. When the anti-allergy benzocycloheptathiophene derivative compound of Formula I is used in combination with an additional therapeutic agent to treat or prevent allergy, an allergic disease or symptoms related thereto in a human patient, the presently disclosed anti-allergy benzocycloheptathiophene derivative compounds of Formula I and additional therapeutic agents can be present in a pharmaceutically or anti-allergy or anti-inflammatory effective amount. By virtue of their additive or synergistic effects, when used in the combinations described above, each can also be present in a subclinical pharmaceutically effective or anti-allergy or anti-inflammatory effective amount, i.e., an amount that, if used alone, provides reduced pharmaceutical effectiveness in completely inhibiting or reducing the production of cytokines or mast cell degranulation and/or reducing or ameliorating conditions or symptoms associated with allergic reaction, inflammation and cytokine overexpression in patients compared to such anti-allergy benzocycloheptathiophene derivative compounds of Formula I and additional therapeutic agents when used in pharmaceutically effective amounts.

While the methods of the present invention can be used to treat or ameliorate the symptoms associated with allergy, allergic disease or airway inflammation, the compounds of the invention can also be used to inhibit or ameliorate one or more inappropriate immune responses or their symptoms in allergy, asthma, autoimmunity, inflammation, or related conditions. The effects of the compounds include detectably ameliorating one or more of (1) the activation and degranulation of mast cells, (2) reducing unwanted cytotoxic immune cell hypersensitivity, (3) reducing unwanted autoantibody or other antibody synthesis, e.g., an unwanted IgA, IgE, IgG or IgM, in allergy, asthma or another autoimmune or inflammation condition, (4) inhibiting the development, proliferation or unwanted activity of autoreactive T or B cells, (5) altering the expression of one or more cytokines, interleukins or cell surface antigens, e.g., a cytokine, interleukin or cell surface antigen described herein, (6) decreasing eosinophilia in allergy conditions, (7) detectably decreasing the level or activity of one or more of ICAM-1, IL-1.alpha., IL-1.beta., TNF.alpha., IL-13, IL-4, IL-6 or IL-8 in, e.g., inflammation conditions or in autoimmune conditions, (8) decreasing the level or biological activity of one or more of TNF, IFN-.gamma., and IL-1, (9) reducing induction of arachidonic acid metabolism or reducing eicosanoid metabolites such as thromboxanes or prostaglandins in, e.g., asthma, (10) reducing IL-4, IL-6, IL-8 or IL-10 synthesis, levels or activity in, e.g., allergy or inflammation such as idiopathic pulmonary fibrosis or allergic asthma or (11) reducing or interfering with neutrophil chemotaxis by, e.g., reducing thioredoxin release from affected cells in conditions such as infections, inflammation or autoimmunity.

In one embodiment, the invention is a method of the prophylaxis or treatment of asthma comprising administering a composition of the invention to a subject in need of such treatment, wherein the amount of the composition is sufficient for the prophylaxis or treatment of asthma in the subject. In asthma, chronic inflammatory processes in the airway play a central role in increasing the resistance to airflow within the lungs. Many cells and cellular elements are involved in the inflammatory process, particularly mast cells, eosinophils, basophils, T-lymphocytes, neutrophils, epithelial cells. The reactions of these cells result in an associated increase in the existing sensitivity and hyper-responsiveness of the airway smooth muscle cells that line the airways to the particular stimuli involved. Therefore, the invention also includes rapidly treating asthma with a compound of the invention, wherein the compound is able to regulate the production of pro-inflammatory mediators from various immune cells. Rapidly treating asthma can mean that the administration of a therapeutically effective dosage of a composition of the invention will result in an observable reduction in at least one symptom of the asthmatic condition in a subject, within 4 hours, or within 3 hours, or within 2 hours, or within 1 hour, or within 30 minutes of administration. In some embodiments, the compounds of the present invention when administered to a subject with asthma and experiencing symptoms of asthma may also provide symptomatic relief of the subject's asthma for periods of time ranging from about 1 hour to about 72 hours, or from about 1 hour to about 48 hours, or from about 1 hour to about 24 hours or from about 1 hour to about 12 hours or from about 1 hour to about 4 hours, or from about 2 hours to about 72 hours, or from about 6 hours to about 72 hours, or from about 12 hours to about 72 hours, or from about 18 hours to about 72 hours, or from about 24 hours to about 72 hours, or from about 48 hours to about 72 hours, or from about 60 hours to about 72 hours after the initial administration of a pharmaceutically effective amount of a composition comprising a compound of Formula I.

Reducing inflammation and edema of the tissue surrounding the airway can also increase the diameter of an airway. Inflammation and edema (accumulation of fluid) of the airway are chronic features of asthma. The inflammation and edema can be reduced by application of a compound of the invention to stimulate wound healing and regenerate normal tissue. Healing of the epithelium or sections of the epithelium experiencing ongoing denudation and renewal allows regeneration of healthy epithelium with less associated airway inflammation. The less inflamed airway has an increased airway diameter both at a resting state and in constriction. Inflammatory mediators released by tissue in the airway wall may serve as a stimulus for airway smooth muscle contraction. Therapy that reduces the production and release of inflammatory mediators can reduce smooth muscle contraction, inflammation of the airways, and edema. Examples of inflammatory mediators are cytokines, chemokines, and histamine. The tissues which produce and release inflammatory mediators include, but are not limited to: airway smooth muscle, epithelium, mast cells, eosinophils and basophils. Treatment of these structures with a compound of the invention can reduce the ability of the airway structures to produce or release pro-inflammatory mediators. The reduction in released inflammatory mediators can reduce chronic inflammation, thereby increasing the airway inner diameter, and may also reduce hyper-responsiveness of the airway smooth muscle.

Without wishing to be bound by any particular theory, it is believed that the compounds of the invention can be used to treat asthma. This is because the compounds of the invention are capable of at least modulating the immune response. Preferably, the method of treating asthma encompasses administering a compound of Table 1 or a pharmaceutically acceptable salt thereof, solvate, or prodrug thereof present in a pharmaceutically acceptable composition, the compound or pharmaceutically acceptable salt thereof, solvate, or prodrug thereof is administered to the subject in an amount from 0.0001 to about 10 mg per kilogram of body weight per day.

Results presented herein demonstrate that the compounds of the invention exhibit a desirable oral bioavailability at a low dose. For example, it was observed that oral administration of a compound of the present invention orally caused a significant block in DNP-induced swelling and increase the weight of the ear and the feet in an animal model, comparable to a known allergy treatment compound, ketotifen and in some assays even surpassing the activity of ketotifen (See foot weight of Compound treated mice in FIG. 3B). These results suggest that the compounds of the present invention as illustrated in Example 7 below, have therapeutic effects on allergic inflammation after allergen challenge in vivo. Thus, invention provides a method of achieving the desired bioavailability of the active ingredient.

In one embodiment, the invention is a method of the prophylaxis or treatment of COPD comprising administering a composition of the invention to a subject in need of such treatment, wherein the amount of the composition is sufficient for the prophylaxis or treatment of COPD in the subject.

In one embodiment, the invention is a method of the prophylaxis or treatment of bronchoconstriction, lung inflammation or lung allergy comprising administering a composition of the invention to a subject in need of such treatment, wherein the amount of the composition is sufficient for the prophylaxis or treatment of bronchoconstriction, lung inflammation or lung allergy in the subject.

The allergic reaction in humans and animals has been extensively studied and the basic immune mechanisms involved are well known. Allergic conditions or diseases in humans include but are not limited to eczema, allergic rhinitis or coryza, hay fever, conjunctivitis, bronchial or allergic asthma, urticaria (hives) and food allergies; atopic dermatitis; anaphylaxis; drug allergy; angioedema; and allergic conjunctivitis. Allergic diseases in dogs include but are not limited to seasonal dermatitis; perennial dermatitis; rhinitis: conjunctivitis; allergic asthma; and drug reactions. Allergic diseases in cats include but are not limited to dermatitis and respiratory disorders; and food allergens. Allergic diseases in horses include but are not limited to respiratory disorders such as "heaves" and dermatitis. Allergic diseases in non-human primates include but are not limited to allergic asthma and allergic dermatitis.

The generic name for molecules that cause an allergic reaction is allergen. There are numerous species of allergens. The allergic reaction occurs when tissue-sensitizing immunoglobulin of the IgE type reacts with foreign allergen. The IgE antibody is bound to mast cells and/or basophils, and these specialized cells release chemical mediators (vasoactive amines) of the allergic reaction when stimulated to do so by allergens bridging the ends of the antibody molecule. Histamine, platelet activating factor, arachidonic acid metabolites, and serotonin are among the best known mediators of allergic reactions in humans. Histamine and the other vasoactive amines are normally stored in mast cells and basophil leukocytes. The mast cells are dispersed throughout animal tissue and the basophils circulate within the vascular system. These cells manufacture and store histamine within the cell unless the specialized sequence of events involving IgE binding occurs to trigger its release.

Accordingly, the compounds of the invention can be used to reduce IgE-mediated mast cell degranulation and related responses at least in part, by decreased production of one or more biological mediators, e.g., substance P neuropeptide, thymus- and activation-regulated chemokine, lipid mediators and cytokines, for example, TNF-α, MCP-1, RANTES, CXCL10, CXCL8 (IL-8), IL-1, IL-3, IL-4, IL-5, IL-6, IL-9, IL-10, IL-13, and IL-23, by one or more other cell types such as eosinophils and other immune cells as described herein.

In one illustrative example, the compounds of the invention can be used to reduce the symptoms, inhibit the asthmatic reaction, or prevent an allergic response. In some embodiments, the compounds of the invention are useful for treating and/or ameliorating the symptoms of both asthma and allergy. In some embodiments, the prophylactic or treatment methods contemplated herein include the use of the compounds of the invention in combination optionally with other suitable therapies or additional therapeutic agents (e.g., asthma/allergy medicament). An additional therapeutic agent as used herein is a composition of matter that reduces the symptoms, inhibits the asthmatic or allergic reaction, or prevents the development of an allergic or asthmatic reaction. In still further embodiments of the method for treating or alleviating the symptoms of an allergic disease or respiratory disease (e.g. asthma), the method also includes administering an anti-allergy benzocycloheptathiophene derivative compound of Formula I or a pharmaceutically acceptable salt thereof, solvate, or prodrug thereof, optionally in combination with an additional therapeutic agent, for example, an anti-inflammatory agent, an antibiotic, a bronchodilator/beta-2 agonist, an adrenergic agonist, a methylxanthine compound, an antihistamine, a prostaglandin inducer, an inhaled glucocorticoid, a systemic glucocorticoid, an immunomodulator, a leukotriene modifier, an IgE blocker, a mast cell stabilizer, an anticholinergic, methotrexate, a PDE-$_4$ inhibitor, a K$^+$ channel opener, a VLA-4 antagonist, a neurokin antagonist, a TXA2 synthesis inhibitor, a xanthanine compound, an arachidonic acid antagonist, a 5-lipoxygenase inhibitor, a thromboxin A2 receptor antagonist, a thromboxane A2 antagonist, an inhibitor of 5-lipoxygenase activation protein, a protease inhibitor and combinations thereof.

Use of such combination provides an improved sustained pharmacologic effect that translates to an improved disease management. For instance, the efficacy of the combination of the compounds of the invention with an additional therapeutic agent is improved over the use of each of the medicaments alone. In some instances, the combination of a compound of the invention with an additional therapeutic agent works in a synergistic manner. In some instances, the combination of a compound of the invention with an additional therapeutic agent works in an additive manner. In some instances, the combination of a compound of the invention with an additional therapeutic agent works to reduce the severity of a side effect inherent in the use of either agent when used alone.

In some embodiments, an additional therapeutic agent comprises a bronchodilator and/or $β_2$ adrenoceptor agonist. Bronchodilator or $β_2$ adrenoceptor agonists are a class of compounds that causes bronchodilation or smooth muscle relaxation. Bronchodilator and/or $β_2$adrenoceptor agonists include, but are not limited to, salmeterol (Serevent™, GlaxoSmithKline), salbutamol, also known as albuterol; Ventolin™/Ventorlin™, GlaxoSmithKline; Asthalin™, Cipla; Proventil™, Schering-Plough; Pro-Air™, Teva), terbutaline (Brethine™/Bricanyl™/Brethaire™), formoterol (Foradil™/Foradile™, Novartis; Oxis™, Astra Zeneca; Atock™, Astellas; Perforomist™, Dey), fenoterol (Berotec™, Boehringer-Ingelheim), bitolterol (Tornalate™, Elan Pharmaceuticals), pirbuterol (Maxair™, 3M), and orciprenaline (Alotec™/Alupent™/Metaprel™/Novasmasol™).

Long-acting $β_2$adrenoceptor agonists and bronchodilators are used for long-term prevention of symptoms in addition to the anti-inflammatory therapies. They cause bronchodilation or smooth muscle relaxation, by activating adenylate cyclase, increasing cyclic AMP and producing functional antagonism of bronchoconstriction. These compounds also inhibit mast cell mediator release, decrease vascular permeability and increase mucociliary clearance. Long-acting $\beta_2$ adrenoceptor agonists include, but are not limited to, salmeterol, also known as albuterol. These compounds are usually used in combination with corticosteroids and generally are not used without any inflammatory therapy. They have been associated with side effects such as tachycardia, skeletal muscle tremor, hypokalemia, and the like. The most common combinations of inhaled steroids and long-acting bronchodilators currently in use are fluticasone/salmeterol (Advair™/Seretide™, GlaxoSmithKline), and budenoside/formoterol (Symbicort™, AstraZeneca).

Short-acting $\beta_2$ adrenoceptor agonists/bronchodilators relax airway smooth muscle, causing the increase in airflow. These classes of compounds are preferred drugs for the treatment of acute asthmatic systems. Short-acting $\beta_2$ adrenoreceptor agonists include, but are not limited to, bitolterol (Tornalate™, Elan Pharmaceuticals), pirbuterol (Maxair™, 3M), and terbutaline (Brethine™/Bricanyl™/Brethaire™). Some of the adverse effects associated with the use of short-acting $\beta_2$ adrenoreceptor agonists include tachycardia, skeletal muscle tremor, hypokalemia, increased lactic acid, headache, and hyperglycemia. Older and less selective adrenergic agonists, such as inhaled epinephrine and ephedrine tablets, have also been used in the treatment of asthma. These agents cause similar or lesser rates of cardiac side effects as albuterol. Inhaled epinephrine may be used to terminate an acute asthmatic exacerbation. These agents may be given parenterally, but adverse effects may arise from this route of administration.

In some embodiments, the additional therapeutic agent can comprise a methylxanthine compound including for instance theophylline (also known as dimethylxanthine; Elixophillin™/Theolair™/Theocin™/Nuelin™/Synophylate™/Bronkodyl™/Aerolate™/Theovent™), doxofylline (Maxivent™/Ansimar™/Ventax™), and aminophylline (Phyllocontin™/Truphylline™/Minomal™), have been used for long-term control and prevention of symptoms. These compounds cause bronchodilation resulting from phosphodiesterase inhibition and likely adenosine antagonism. It is also believed that these compounds may effect eosinophilic infiltration into bronchial mucosa and decrease T-lymphocyte numbers in the epithelium. Dose-related acute toxicities are a particular problem with these compounds. As a result, routine serum concentration must be monitored in order to account for the toxicity and narrow therapeutic range arising from individual differences in metabolic clearance. Side effects include tachycardia, nausea and vomiting, tachyarrhythmias, central nervous system stimulation, headache, seizures, hematemesis, hyperglycemia and hypokalemia.

Other asthma/allergy additional therapeutic agents can be used in combination with the compounds of the invention to treat allergy. Additional therapeutic agents useful in the treatment of allergy include, but are not limited to, anti-histamines, prostaglandin inducers, and steroids.

In some embodiments the additional therapeutic agent is an anti-histamine agent. Anti-histamines counteract histamine released by mast cells or basophils. These compounds are well known in the art and commonly used for the treatment of allergy. Anti-histamines include, but are not limited to, loratidine (Claritin™/Claritin-D™, Schering-Plough; Alayert™, Wyeth), cetirizine (Zyrtec™/Reactine™, Pfizer) and analogues, buclizine Vibazine™/Histabutizine™/Buclifen™/Buclodin™/Longifene), fexofenadine (Allegra™/Telfast™, Sanofi-Aventis), terfenadine (Seldane™, Schering-Plough), desloratadine (NeoClarityn™/Claramax™/Clarinex™/Aerius™, Schering-Plough), norastemizole (Soltara™, Sepracor), epinastine (Elestat™/Relestat™, Allergan), ebastine (Kestine™/Evastin™/Ebastel™/Aleva™, Pharmacare), astemizole (Hismanal™, Janssen), levocabastine (Livostin™, Janssen), azelastine (Astelin™, Meda), tranilast (Rizaben™), mizolastine (Mizollen™), betahistine (SERC™), and the like.

In some embodiments, the additional therapeutic agent can comprise a prostaglandin. Prostaglandin inducers are compounds that induce prostaglandin activity, regulating smooth muscle relaxation. An example of a prostaglandin inducer is rebamipide.

The additional therapeutic agents useful in combination with the compounds of the invention also include steroids and immunomodulators. Glucocorticoids are a class of steroid hormones characterised by an ability to bind with the glucocorticoid receptor (GR) and trigger similar effects. Glucocorticoids are distinguished from mineralocorticoids and sex steroids by their specific receptors, target cells, and effects. In technical terms, corticosteroid refers to both glucocorticoids and mineralocorticoids (as both are mimics of hormones produced by the adrenal cortex), but is often used as a synonym for glucocorticoid. In this document, glucocorticoid and corticosteroid are used interchangeably.

In some embodiments, the additional therapeutic agent can comprise a corticosteroid. Corticosteroids are used long-term to prevent development of the symptoms, and suppress, control, and reverse inflammation arising from an initiator. Some corticosteroids can be administered by inhalation and others are administered systemically. The corticosteroids that are inhaled have an anti-inflammatory function by blocking late-reaction allergen and reducing airway hyper-responsiveness. These drugs also inhibit cytokine production, adhesion protein activation, and inflammatory cell migration and activation. They are also believed to reverse $\beta_2$-receptor downregulation and to inhibit microvascular leakage.

Corticosteroids are used generally for moderate to severe exacerbations to prevent the progression, reverse inflammation and speed recovery from the disease. Cortosteroids are associated with reversible abnormalities in glucose metabolism, increased appetite, fluid retention, weight gain, mood alteration, hypertension, peptic ulcer, and rarely asceptic necrosis of femur. These compounds are useful for short-term (e.g., 3-10 days) prevention of the inflammatory reaction in inadequately controlled persistent asthma. They also function in a long-term prevention of symptoms in severe persistent asthma to suppress and control and actually reverse inflammation. The side effects associated with systemic corticosteroids are even greater than those associated with inhaled corticosteroids. Some side effects associated with longer term use include adrenal axis suppression, growth suppression, dermal thinning, hypertension, diabetes, Cushing's syndrome, cataracts, muscle weakness, and in rare instances, impaired immune function.

The combination of the compounds of the invention and steroids are particularly well suited to the treatment of young subjects (e.g., children). To date, the use of steroids in children has been limited by the observation that some steroid treatments have been reportedly associated with growth retardation. Thus, according to the present invention, the compounds of the invention can be used in combination with steroids, allowing for the use of lower required doses of steroids.

Corticosteroids include, but are not limited to, beclomethasone dipropionate (inhaler: Becotive™/Qvar™; nasal spray: Beconase™/Vancenase™), budesonide (Rhinocort™/Pulmicort™, AstraZeneca), flunisolide (AeroBid™/Nasaline™/

Nasarel™), fluticasone propionate (Flovent™/Flonase™, GlaxoSmithKline; Flixotide™/Flixonase™, Allen & Hanburys), fluticasone furoate (Veramyst™, GlaxoSmithKline) and triamcinolone (Kenalog™/Aristocort™/Nasacort™/Tri-Nasal™/Triderm™/Azmaco-rt™/Trill™/Volon A™/Tristoject™/Fougera™/Tricortl™/Triesence™). Although dexamethasone is a corticosteroid having anti-inflammatory action, it is not regularly used for the treatment of asthma/allergy in an inhaled form because it is highly absorbed, it has long-term suppressive side effects at an effective dose. Dexamethasone, can be used according to the invention for the treating of asthma/allergy because, when administered in combination with the compounds of the invention, it can be administered at a low dose thereby reducing the side effects. Additionally, the compounds of the invention can be administered to reduce the side effects of dexamethasone even at higher concentrations. Some of the side effects associated with corticosteroid include cough, dysphonia, oral thrush (candidiasis), and in higher doses, systemic effects, such as adrenal suppression, osteoporosis, growth suppression, skin thinning and easy bruising.

Systemic corticosteroids include, but are not limited to, methylprednisolone (Medrol™/Solu-Medrol™, Sandoz), prednisolone (Teva, KV Pharmaceutical) and prednisone (Deltasoneprednisone™, Pharmacia & UpJohn).

Inhaled glucocorticoids are the most widely used prevention medications and normally come as inhaler devices: ciclesonide (Alvesco™, Nycomed), beclomethasone (inhaler: Becotive™/Qvar™; nasal spray: Beconase™/Vancenase™), budesonide (Rhinocort™/Pulmicort™, AstraZeneca), flunisolide (AeroBid™/Nasaline™/Nasarel™), fluticasone (Flovent™/Flonase™/Veramyst™, GlaxoSmithKline; Flixotide™/Flixonase™, Allen & Hanburys), mometasone (Naslx™/Asmanex Twisthaler™, Schering-Plough), and triamcinolone (Kenalog™/Aristocort™/Nasacort™/Tri-Nasal™/Triderm™/Azmaco-rt™/Trill™/Volon A™/Tristoject™/Fougera™/Tricortl™/Triesence™). Due to the deleterious side effects of use of corticosteroids, inhaled steroids are generally used for prevention, as their smaller doses are targeted to the lungs, unlike the higher doses of oral preparations.

In some embodiments, the additional therapeutic agent can comprise an immunomodulator. Immunomodulators include, but are not limited to, anti-inflammatory agents, leukotriene antagonists, IL-4 muteins, soluble IL-4 receptors, immunosuppressants, anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, downregulators of IgE, and the like.

In some embodiments, the additional therapeutic agent can comprise a leukotriene modifier. Leukotriene modifiers are often used for long-term control and prevention of symptoms in mild persistent asthma. Leukotrienes are biochemical mediators that are released from mast cells, eosinophils, and basophils that cause contraction of airway smooth muscle and increase vascular permeability, mucous secretions and activate inflammatory cells in the airways of patients with asthma. Leukotriene modifiers function as leukotriene receptor antagonists by selectively competing for LTD-4 and LTE-4 receptors. These compounds include, but are not limited to, montelukast (Singulair™, Merck), zafirlukast (Accolate™/Accoleit™/Vanticon™, AstraZeneca), pranlukast and zileuton (Zyflo™, Abbott). Zileuton tablets function as 5-lipoxygenase inhibitors.

In some embodiments, the additional therapeutic agent can comprise a down-regulator of IgE. Down-regulators of IgE include peptides or other molecules with the ability to bind to the IgE receptor and thereby prevent binding of antigen-specific IgE. Another type of down-regulator of IgE is a monoclonal antibody directed against the IgE receptor-binding region of the human IgE molecule. Thus, one type of down-regulator of IgE is an anti-IgE antibody or antibody fragment. One of skill in the art can prepare functionally active antibody fragments of binding peptides with the same function. Other types of IgE down-regulators are polypeptides capable of blocking the binding of the IgE antibody to the Fc receptors on the cell surfaces and displacing IgE from binding sites upon which IgE is already bound. An example of an IgE blocker is omalizumab (Xolair™), a recombinant DNA-derived IgGlk monoclonal antibody that binds selectively to IgE and is made by Genentech/Novartis.

In some embodiments, the additional therapeutic agent can comprise a mast cell stablizier. Mast cell stabilizers, as the name implies, stabilize mast cell membranes and inhibit activation and release of mediators from eosinophils and epithelial cells. Such compounds, exemplified by cromolyn sodium (cromoglicic acid; nasal spray: Rynacrom™ (UK), Nasalcrom™, Prevalin™ (Netherlands); inhaler: Intal™; oral form: Gastrocrom™) and nedocromil (inhaler: Tilade™; eye drop: Alocril™), are used as long-term control medications for preventing primarily asthma symptoms arising from exercise or allergic symptoms arising from allergens. These compounds are believed to block early and late reactions to allergens by interfering with chloride channel function.

In some embodiments, the additional therapeutic agent can comprise an anticholinergic agent. An anticholinergic agent is a substance that blocks the neurotransmitter acetylcholine in the central and the peripheral nervous system. Frequently, they reduce the effects mediated by acetylcholine on acetylcholine receptors in neurons through competitive inhibition. Therefore, their effects are reversible. Anticholinergics are classified according to the receptors that are affected: (a) antimuscarinic agents operate on the muscarinic acetylcholine receptors; the majority of anticholinergic drugs are antimuscarinics; and (b) antinicotinic agents operate on the nicotinic acetylcholine receptors. Anticholinergics are generally used for the relief of acute bronchospasm. These compounds are believed to function by competitive inhibition of muscarinic cholinergic receptors. Anticholinergics include, but are not limited to, ipratrapoium bromide (Atrovent™/Apovent™, Boehringer Ingelheim), oxitropium and tiotropium (Spiriva™, Boehringer-Ingelheim/Pfizer). These compounds reverse only cholinerigically-mediated bronchospasm and do not modify any reaction to antigen. Side effects include drying of the mouth and respiratory secretions, increased wheezing in some individuals, blurred vision if sprayed in the eyes. Ipratropium is also combined with albuterol (trade names Combivent™ and DuIb™) for the management of chronic obstructive pulmonary disease (COPD) and asthma, and with fenoterol (trade names Duovent™ and Berodual N™) for the management of asthma.

In some embodiments, the additional therapeutic agent can comprise methotrexate. Methotrexate is an antimetabolite and antifolate drug used in treatment of cancer and autoimmune diseases. It acts by inhibiting the metabolism of folic acid. It has come into use as a treatment for some autoimmune diseases, including ankylosing spondylitis, Crohn's disease, psoriasis, psoriatic arthritis, rheumatoid arthritis, and scleroderma, along with difficult-to-treat asthma cases.

In some embodiments, useful additional therapeutic agents which can be combined with a compound of Formula I can include: $\beta_2$-agonists including albuterol, levalbuterol, pirbuterol, artformoterol, formoterol, salmeterol, salbutamol, terbutaline, bitolterol, fluticasone, budesonide and anticholinergics including ipratropium, ipratropium bromide, oxitropium and tiotropium; corticosteroids, glucocorticoids including oral, systemic and inhaled glucocorticoids and including beclomethasone, budesonide, flunisolide, fluticasone, mometasone, triamcinolone, methyprednisolone, prednisolone, prednisone, ciclesonide; leukotriene modifiers including montelukast, zafirlukast, pranlukast and zileuton; mast cell stabilizers including cromolyn and nedocromil; epinephrine, ephedrine, methylxanthines including theophylline, aminophylline, combination drugs including ipratropium and albuterol, fluticasone and salmeterol, budesonide and formoterol; antihistamines including hydroxyzine, rupatadine, diphenhydramine, ketotifen, norketotifen, loratadine, cetirizine, and hydrocortisone; immune system modulating drugs including tacrolimus and pimecrolimus; cyclosporine; azathioprine; mycophenolatemofetil; IgE blockers including omalizumab, and combinations thereof.

In some embodiments, a method for treating an allergic disease in a subject having a known allergen sensitivity can include the administration of a compound of Formula I in combination with an injection of increasing doses of the known allergen to induce tolerance to the allergen and to prevent further allergic reactions. Allergen injection therapy (allergen immunotherapy) is known to reduce the severity of allergic rhinitis. While it is possible for allergen injection therapy to be associated with the risk of side effects such as anaphylactic shock, the use of a composition of the invention and optionally an additional therapeutic agent known in the treatment of the allergy in question, in combination with an allergen can avoid many of the side effects.

In some cases the subject is exposed to an allergen, an allergen inducing solution, or an allergen extract in addition to being treated with a composition of the invention either in the absence or presence of the optional additional therapeutic agent. In this particular method, the subject is said to be exposed to the allergen, allergen inducing solution, or allergen extract. As used herein, the term "exposed to" refers to either the active step of contacting the subject with an allergen or the passive exposure of the subject to the allergen, allergen inducing solution, or allergen extract in vivo. Methods of the active exposure of a subject to an allergen are well-known in the art. In general, an allergen, an allergen inducing solution, or an allergen extract is administered directly to the subject by any means such as intravenous, intramuscular, oral, transdermal, mucosal, intranasal, intratracheal, or subcutaneous administration. The allergen, allergen inducing solution, or allergen extract can be administered systemically or locally. A subject is passively exposed to an allergen, an allergen inducing solution, or an allergen extract if the allergen, allergen inducing solution, or allergen extract becomes available for exposure to the immune cells in the body. A subject may be passively exposed to an allergen, an allergen inducing solution, or an allergen extract, for instance, by entry of an allergen into the body when the allergen is present in the environment surrounding the subject, i.e. pollen.

As used herein, the term "prevent", "prevented", or "preventing" when used with respect to the treatment of an allergic or asthmatic disorder refers to a prophylactic treatment which increases the resistance of a subject to an allergen, in other words, decreases the likelihood that the subject will develop an allergic or asthmatic response to the allergen as well as a treatment after the allergic or asthmatic disorder has begun in order to fight the allergy/asthma, e.g., reduce or eliminate it altogether or prevent it from becoming worse.

In another aspect, the invention includes a method of decreasing the dose of an additional therapeutic agent by administering to a subject having asthma or allergy or at risk of developing asthma or allergy an additional therapeutic agent in a sub-therapeutic dosage in combination with a compound of the invention, wherein the combination of the sub-therapeutic dose of the additional therapeutic agent and the compound of the invention produce a therapeutic result in the prevention or treatment of asthma or allergy in the subject. The method allows a lower dose of the additional therapeutic agent to be used. This provides several advantages, including lower costs associated with using less drugs and less chances of inducing side effects resulting from the medications by using lower doses.

According to other aspects, the invention provides methods of treating or preventing asthma and/or allergy by administering a compound of the invention and an additional therapeutic agent in different dosing schedules. In one aspect, the invention is a method of preventing or treating asthma or allergy by administering to a subject a compound of the invention in an effective amount for modulating the immune response and subsequently administering to the subject an additional therapeutic agent. In other aspects, the invention is a method of preventing or treating asthma or allergy by administering to a subject an additional therapeutic agent in an effective amount for providing some symptomatic relief and subsequently administering a compound of the invention to the subject.

Kits

The present invention also provides a kit comprising a composition of the invention and a delivery device. The compositions may conveniently be presented in single or multiple unit dosage forms as well as in bulk, and may be prepared by any of the methods which are well known in the art of pharmacy. The composition, found in the kit, is already formulated together, or in the kit the compounds are separately provided along with other ingredients, and instructions for its formulation and administration regime. The kit may also contain other agents, such as those described elsewhere herein and, for example, when for parenteral administration, they may be provided with a carrier in a separate container, where the carrier may be sterile. The present composition may also be provided in lyophilized form, and in a separate container, which may be sterile, for addition of a liquid carrier prior to administration.

In a specific embodiment, the kit of the present invention comprises a compound of the invention, an applicator, and an instructional material for the use thereof. In another embodiment, the kit can comprise a compound of formula I, such as those described elsewhere herein, a container holding the compound, and an instructional material. The skilled artisan can provide the applicator.

Preferably, the kit of the present invention comprises a compound of formula I, a compound of Formula Ia, or a compound of Table 1, or combinations thereof. More preferably, the kit comprises Compound A. Additionally, the kit can comprise an instructional material and an applicator for the administration of the compound(s) of the present invention for the treatment of allergy or an allergic or respiratory disease or condition. The kits of the present invention can be used to treat the diseases and conditions disclosed herein. The kits described in the present invention are not limited to the uses above however, and can be used in any method derived from the teachings disclosed herein.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLES

Example 1

Synthesis of 4-[1-(5-methyl-pyridin-3-ylmethyl)piperidin-4-ylidene]-4,9-dihydro-1-thia-benzo[f]azulen-10-one

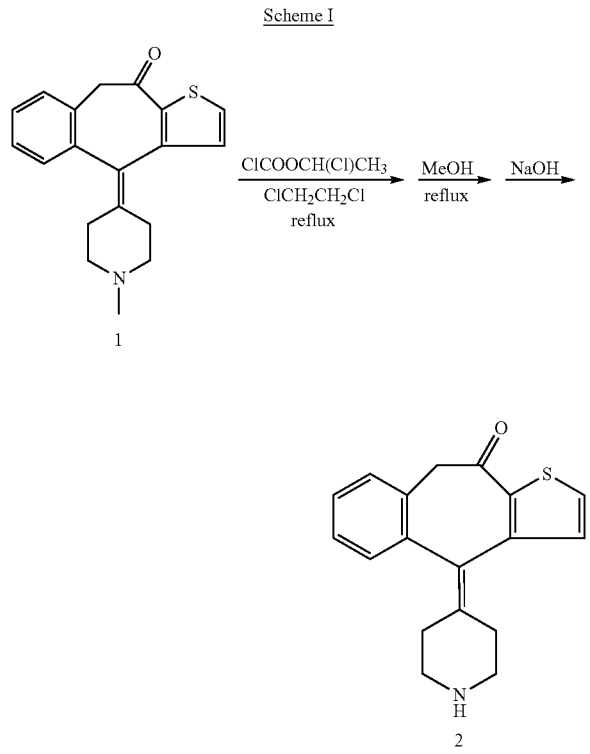

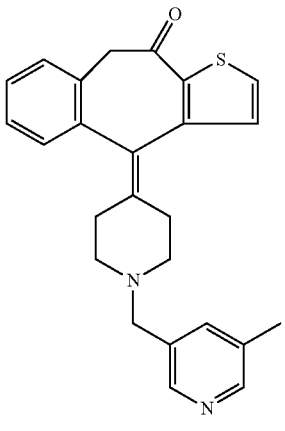

Scheme I gives 4-[1-(5-methyl-pyridin-3-ylmethyl)piperidin-4-ylidene]-4,9-dihydro-1-thia-benzo[f]azulen-10-one (5) by alkylation of norketotifen (2) with 3-Bromomethyl-5-methyl-pyridine (4). Compound (4) was obtained by treatment of 3,5-lutidine (3) with NBS and AIBN in a solvent mixture of chloroform and carbon tetrachloride. Norketotifen (2) was obtained by treatment of ketotifen with 1-chloroethyl chloroformate and methanol respectively. Norketotifen (2) can also be obtained by treatment of ketotifen with vinyl chloroformate. Similarly, Norketotifen (2) can be obtained by treatment of ketotifen with 2,2,2-trichloroethyl chloroformate (see U.S. Pat. No. 7,557,128). Alternatively, Norketotifen (2) can be obtained by treatment of ketotifen with cyanogen bromide (von Braun dealkylation) or ethyl chloroformate (see Helvetica Chimica Acta 1976, 59(3), 876), followed by subsequent hydrolysis in basic or acidic aqueous solutions.

Example 2

Synthesis of 4-[1-(5-methyl-pyridin-3-ylmethyl)piperidin-4-ylidene]-4,9-dihydro-1-thia-benzo[f]azulen-10-one. (Synthesis Scheme II)

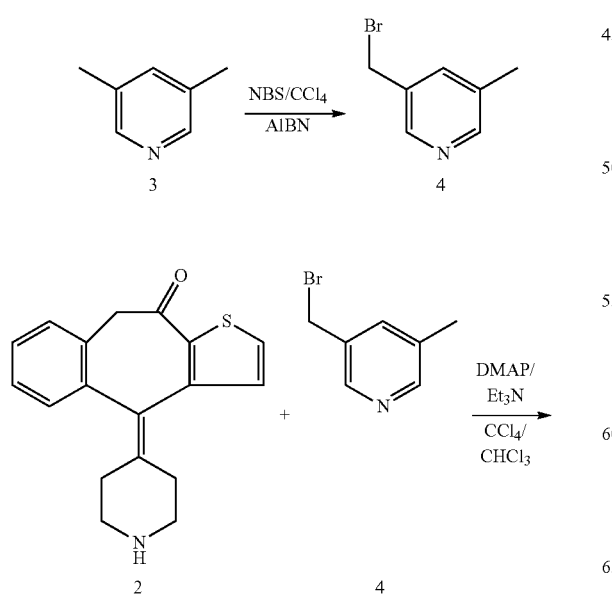

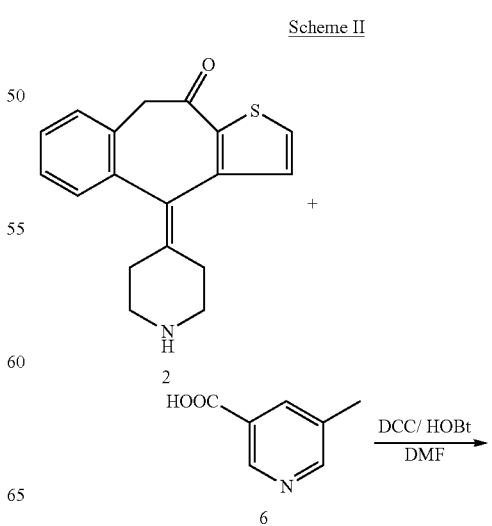

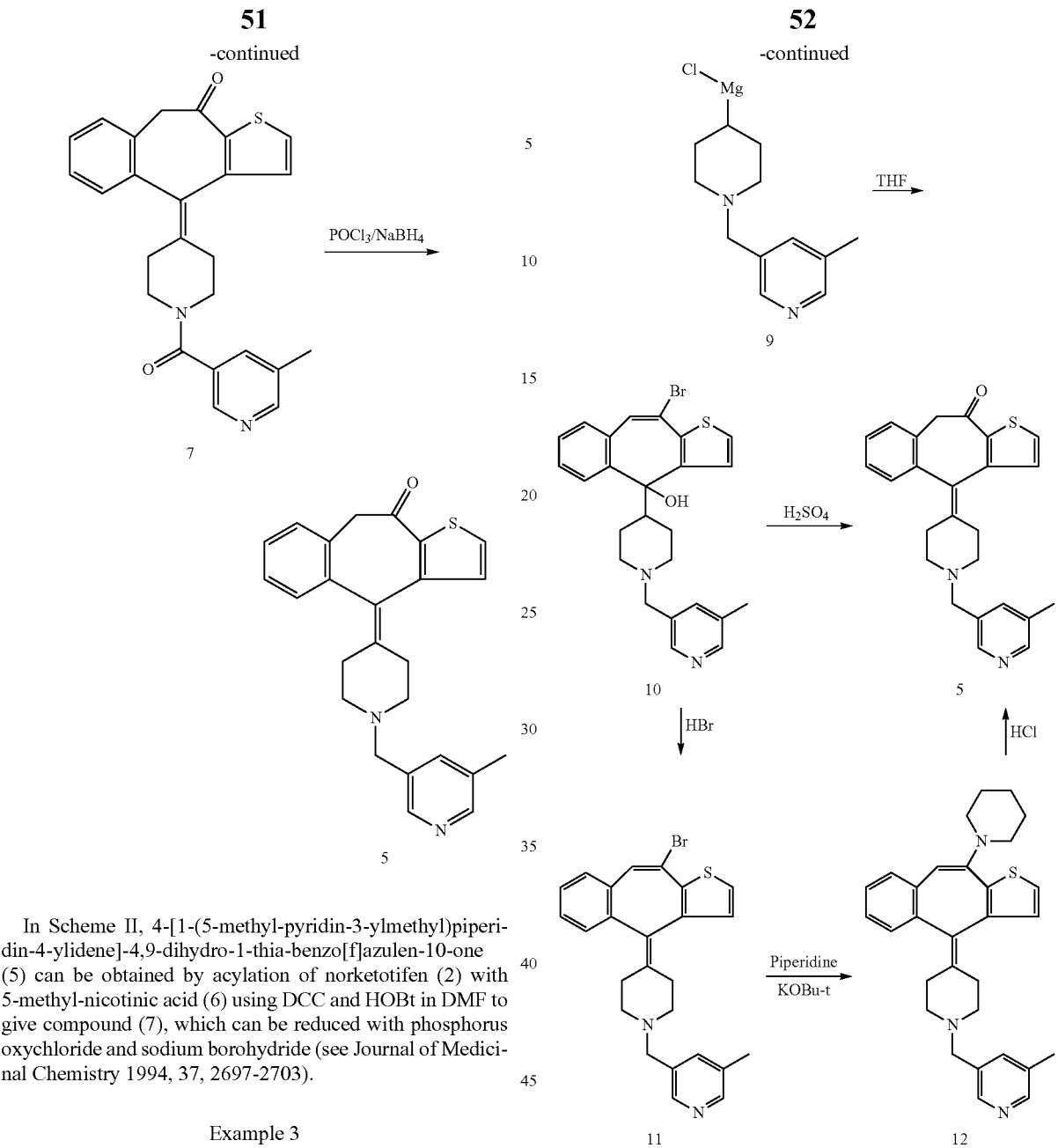

In Scheme II, 4-[1-(5-methyl-pyridin-3-ylmethyl)piperidin-4-ylidene]-4,9-dihydro-1-thia-benzo[f]azulen-10-one (5) can be obtained by acylation of norketotifen (2) with 5-methyl-nicotinic acid (6) using DCC and HOBt in DMF to give compound (7), which can be reduced with phosphorus oxychloride and sodium borohydride (see Journal of Medicinal Chemistry 1994, 37, 2697-2703).

Example 3

Synthesis of 4-[1-(5-methyl-pyridin-3-ylmethyl) piperidin-4-ylidene]-4,9-dihydro-1-thia-benzo[f]azulen-10-one. (Synthesis Scheme III)

Scheme III

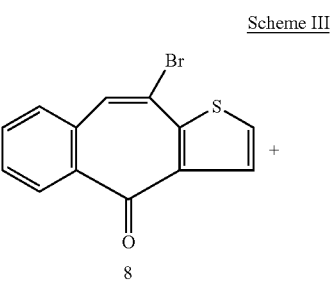

In Scheme III, reaction of compound (8) with the Grignard derivative (9) prepared from 3-(4-chloro-piperidin-1-ylmethyl)-5-methyl-pyridine (See Reference: Drugs of the Future 1996, 21(10):1032-1036 and Spanish Patent ES 2120899) affords alcohol (10), which is finally eliminated HBr and dehydrated by $H_2SO_4$ to give 4-[1-(5-methyl-pyridin-3-ylmethyl)piperidin-4-ylidene]-4,9-dihydro-1-thia-benzo[f]azulen-10-one (5). Alternatively, dehydration of alcohol (10) by HBr gives compound (II), which is treated with piperidine and potassium t-butoxide to afford compound (12). Treatment of compound (12) with aqueous hydrochloride gives 4-[1-(5-methyl-pyridin-3-ylmethyl)piperidin-4-ylidene]-4,9-dihydro-1-thia-benzo[f]azulen-10-one (5). Compound (8) can be prepared according to Helvetica Chimica Acta (1976), 59(3):876-877.

Example 4

Synthesis of 4-[1-(5-methyl-pyridin-3-ylmethyl) piperidin-4-ylidene]-4,9-dihydro-1-thia-benzo[f] azulen-10-one. (Synthesis Scheme IV)

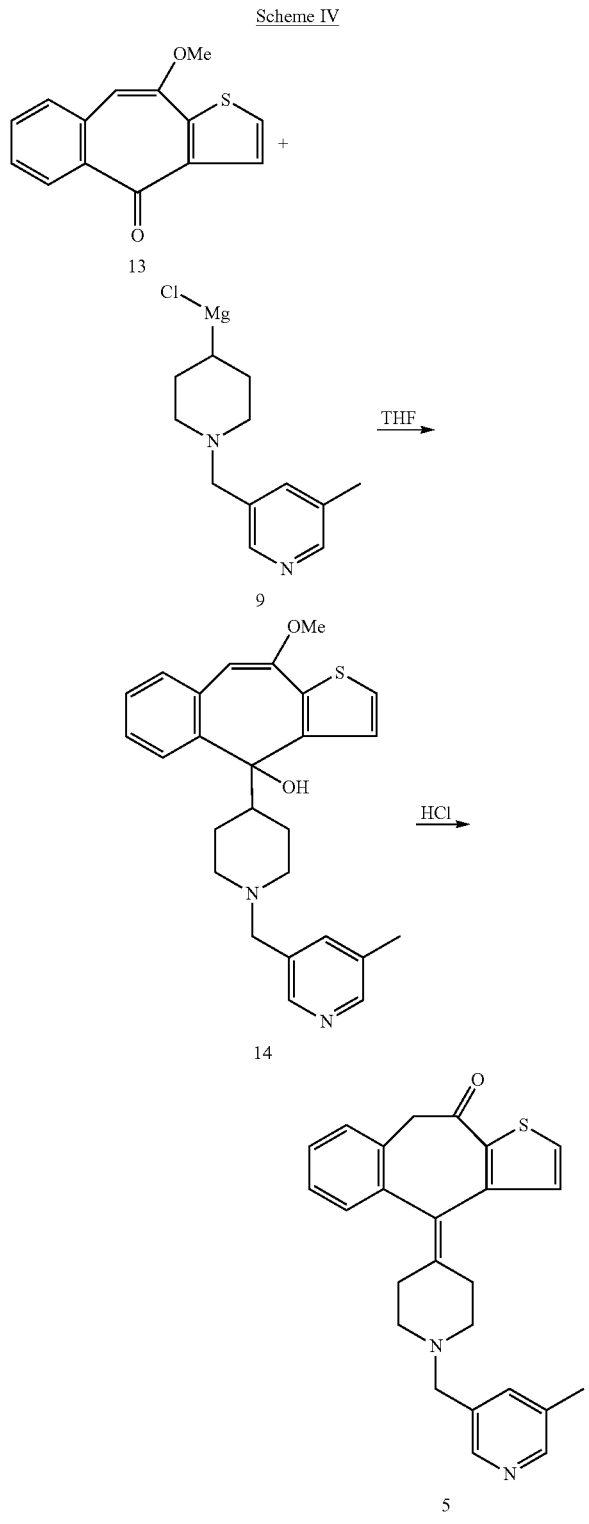

In Scheme IV, 4-[1-(5-methyl-pyridin-3-ylmethyl)piperidin-4-ylidene]-4,9-dihydro-1-thia-benzo[f]azulen-10-one (5) could be synthesized by reaction of compound (13) with the Grignard derivative (9) to give alcohol (14), which is treated with aqueous hydrochloride to afford 4-[1-(5-methyl-pyridin-3-ylmethyl)piperidin-4-ylidene]-4,9-dihydro-1-thia-benzo[f]azulen-10-one (5). Compound (13) can be prepared according to Helvetica Chimica Acta (1976), 59(3):876-877.

Example 5

Prophylactic effects of 4-[1-(5-methyl-pyridin-3-ylmethyl)piperidin-4-ylidene]-4,9-dihydro-1-thia-benzo[f]azulen-10-one on allergy in vivo: IgE-mediated late phase cutaneous reactions (Ear and foot swelling)

Mice were given 4-[1-(5-methyl-pyridin-3-ylmethyl)piperidin-4-ylidene]-4,9-dihydro-1-thia-benzo[f]azulen-10-one (1 mg/kg) or ketotifen (1 mg/kg) orally twice as per the schedule dosing regimen provided in FIG. 1A as indicated by the numbered dose in a circle. The first dose (indicated by a circled number 1) was given on day 1 before IgE injection and a 2nd dose (indicated by a circled number 2) was given on day 2 before dinitrofluorobenzene (DNFB, as an allergen) challenge. Mice were passively sensitized by i.v. injection of 2 µg anti-DNP IgE mAb (Sigma). After 24 h, a cutaneous reaction was elicited by the application of 20 µl of DNFB (0.3% wt/vol, Sigma) in acetone-olive oil (4:1) to both sides of the left hind paw or left ear, and 20 µl of acetone-olive oil to the right hind paw or right ear as a control. The thickness of foot pad or ear was measured using a digital micrometer after 24 h. The thickness of the right ear or right hind paw (treated with acetone-olive oil only) was used as baseline values. The DNFB-induced increment of tissue thickness was expressed as the percentage of the baseline values.

Figure 1B:
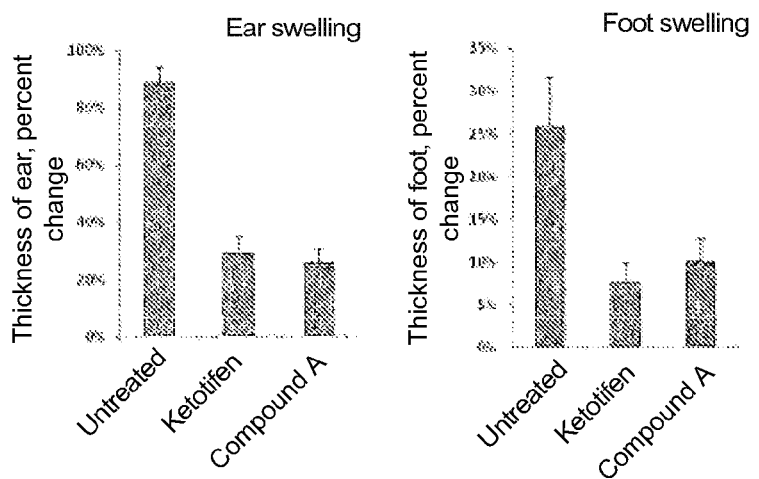
FIG. 1B depicts graphical representation of the anti-allergy effects of Compound A on ear and foot swelling in vivo experiments.

In this animal model, ear and foot swelling are largely induced by cytokines and chemokines released from mast cells. Administration of 4-[1-(5-methyl-pyridin-3-ylmethyl)piperidin-4-ylidene]-4,9-dihydro-1-thia-benzo[f]azulen-10-one strongly reduced allergen DNFB-induced ear and foot swelling as shown in FIG. 1B. This finding suggests that 4-[1-(5-methyl-pyridin-3-ylmethyl)piperidin-4-ylidene]-4,9-dihydro-1-thia-benzo[f]azulen-10-one inhibits mast cell-mediated late-phase allergic inflammation likely through inhibiting mast cell cytokine and chemokine production.

Example 6

Prophylactic effects of 4-[1-(5-methyl-pyridin-3-ylmethyl)piperidin-4-ylidene]-4,9-dihydro-1-thia-benzo[f]azulen-10-one on allergy in vivo: IgE-mediated passive cutaneous anaphylaxis (Evan's blue dye leakage)

Figure 2A:
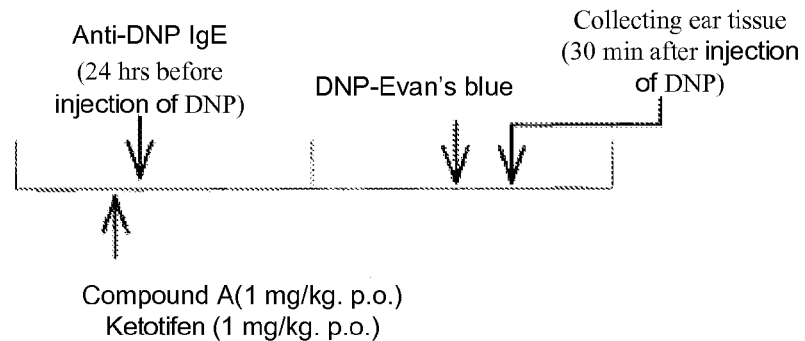
FIG. 2A depicts the treatment schedule for anti-histamine and mast cell stabilization testing in vivo using dinitrophenyl (DNP) using the Evan's blue leakage protocol and inhibition of allergic responses with ketotifen and Compound A in mice.

Mice were given 4-[1-(5-methyl-pyridin-3-ylmethyl)piperidin-4-ylidene]-4,9-dihydro-1-thia-benzo[f]azulen-10-one (1 mg/kg) or ketotifen (1 mg/kg) orally as per dosing schedule shown in FIG. 2A. Subsequently, mice were sensitized by intradermal injection of 20 ng antidinitrophenyl (DNP) IgE mAb (Sigma) into left ears, while right ear received saline as a control. After 24 h, mice were challenged by i.v. injection of 100 µg of DNP-Bovine Serum Albumin (BSA) (as an allergen) in 200 µl Evan's blue dye (1% wt/vol, Sigma). Thirty min later, ear punch (8 mm) was collected in 300 µl of formamide and incubated at 80° C. for 2 h in water bath to extract Evan's blue dye. The absorbance was determined at 620 nm.

Figure 2B:
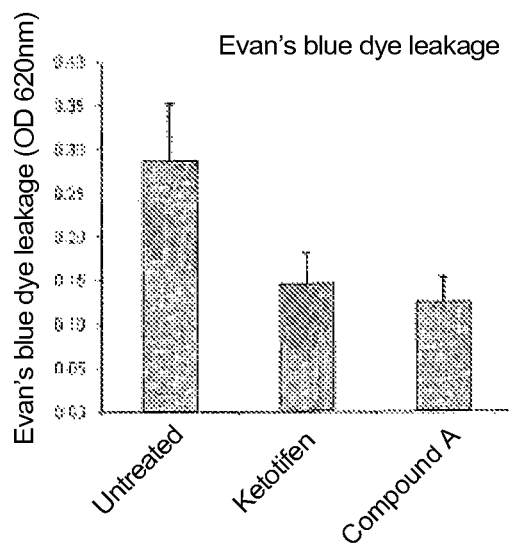
FIG. 2B depicts graphical representation of the inhibitory effects of Compound A against mast cell mediator-induced vascular permeability in vivo.

In this mice model, the Evan's blue dye leakage is largely induced by mast cell granule associated mediators such as histamine. Granule-associated mediators such as histamine stimulate endothelium and blood vessel smooth muscle cells leading to increased vascular permeability. Administration of 4-[1-(5-methyl-pyridin-3-ylmethyl)piperidin-4-ylidene]-4,9-dihydro-1-thia-benzo[f]azulen-10-one strongly reduced allergen (DNP)-induced Evan's blue dye leakage when compared to the vehicle control shown in FIG. 2B. It is important to note that the inhibitory effects on both Evan's blue dye leakage and tissue swelling were observed 24 hours after oral administration of 4-[1-(5-methyl-pyridin-3-ylmethyl)piperidin-4-ylidene]-4,9-dihydro-1-thia-benzo[f]azulen-10-one, suggesting long-lasting effects of this chemical compound.

Example 7

Therapeutic effects of 4-[1-(5-methyl-pyridin-3-ylmethyl)piperidin-4-ylidene]-4,9-dihydro-1-thia-benzo[f]azulen-10-one on allergy in vivo: IgE-mediated late phase cutaneous reactions (Ear and foot swelling)

Figure 3A:
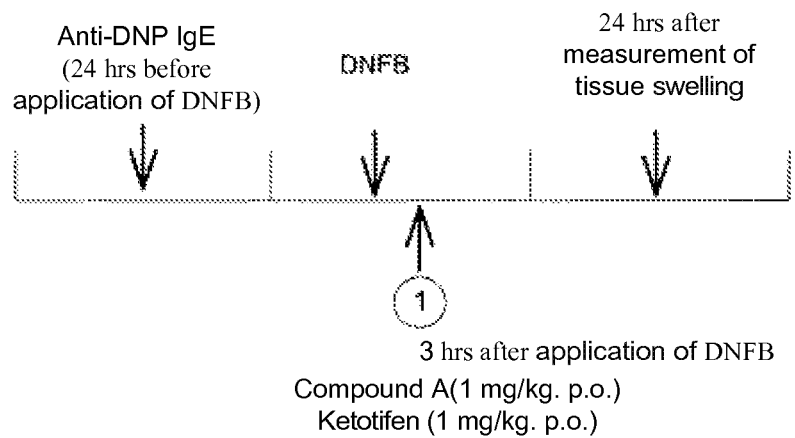
FIG. 3A depicts a dosing schedule for testing the anti-allergy effects of Compound A in an in vivo DNFB challenge model measuring IgE-mediated late phase cutaneous reactions.

To demonstrate the therapeutic effects in vivo of 4-[1-(5-methyl-pyridin-3-ylmethyl)piperidin-4-ylidene]-4,9-dihydro-1-thia-benzo[f]azulen-10-one, mice were passively sensitized by i.v. injection of 2 μg anti-DNP IgE mAb. After 24 h, a cutaneous reaction was elicited by the application of 20 μL of DNFB (0.3% wt/vol, Sigma) in acetone-olive oil (4:1) to both sides of the left hind paw or left ear, and 20 μl of acetone-olive oil to the right hind paw or right ear as a control as shown in FIG. 3A. Three hours after DNFB application, mice were given 4-[1-(5-methyl-pyridin-3-ylmethyl)piperidin-4-ylidene]-4,9-dihydro-1-thia-benzo[f]azulen-10-one (1 mg/kg, p.o.), ketotifen (1 mg/kg, p.o.) or saline as control as indicated in FIG. 3A by the circled number "1". The thickness of foot pad or ear was measured using a digital micrometer after 24 h of DNFB application. The weight of hind paw or ear punch (5 mm) was also determined. The thickness and weight of the right ear or right hind paw (treated with acetone-olive oil only) were used as baseline values. The DNFB-induced increment of tissue thickness was expressed as the percentage of the baseline values.

Figure 3B:
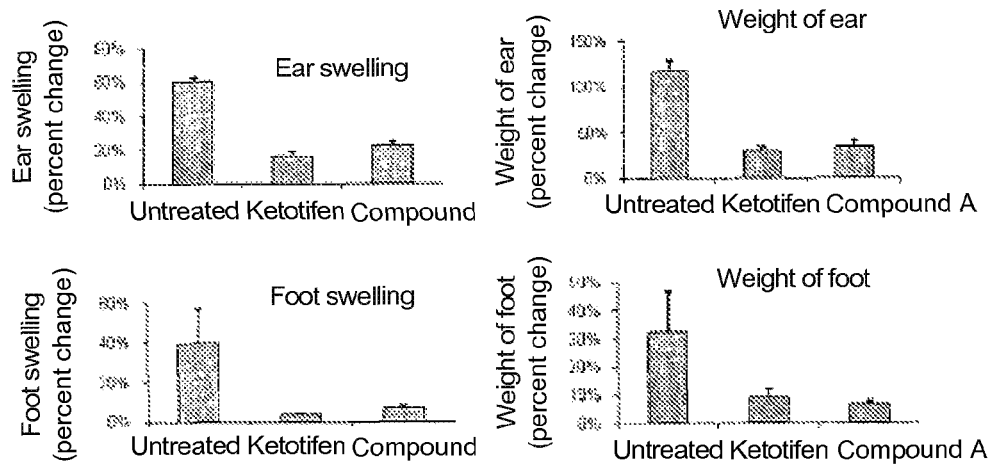
FIG. 3B depicts graphic representation of the anti-allergic effects of Compound A in an in vivo mouse IgE-mediated late phase cutaneous challenge using DNFB in pre-sensitized mice.

As shown in FIG. 3B, application of 4-[1-(5-methyl-pyridin-3-ylmethyl)piperidin-4-ylidene]-4,9-dihydro-1-thia-benzo[f]azulen-10-one after antigen DNP challenge was found to significantly block DNP-induced swelling and increase the weight of the ear and the feet in this animal model, comparable to ketotifen and in some assays even surpassing the activity of ketotifen (See foot weight of Compound treated mice in FIG. 3B). These results suggest that 4-[1-(5-methyl-pyridin-3-ylmethyl)piperidin-4-ylidene]-4,9-dihydro-1-thia-benzo[f]azulen-10-one has therapeutic effects on allergic inflammation after allergen challenge in vivo.

Example 8

Figure 4:
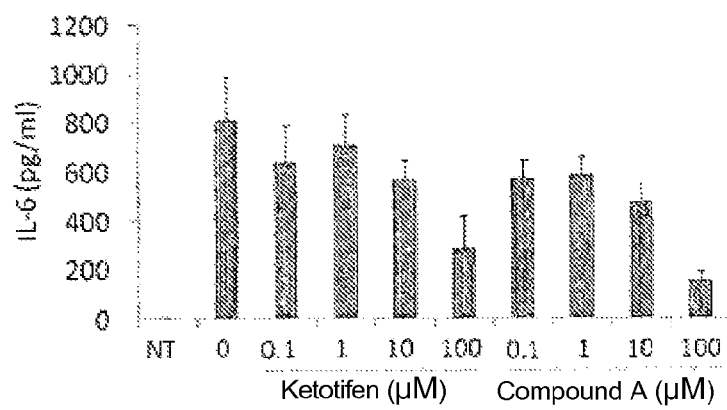
FIG. 4 depicts cytokine (IL-6) expressing inhibitory activity of Compound A in sensitized mouse bone marrow derived mast cells stimulated with trinitrophenol-bovine serum albumin (TNP-BSA).

4-[1-(5-methyl-pyridin-3-ylmethyl)piperidin-4-ylidene]-4,9-dihydro-1-thia-benzo[f]azulen-10-one inhibits allergen-induced cytokine IL-6 production by mast cells in vitro Mouse bone marrow derived mast cells (BMMCs) were resuspended in fresh complete medium supplemented with TIB141-conditioned medium enriched in IgE directed against trinitrophenyl (TNP) at a ratio of 3:1. BMMCs were typically sensitized at 0.5 million/ml. Following sensitization, BMMCs were washed extensively with RPMI 1640 supplemented with 10% FBS alone. BMMCs were then treated with 4-[1-(5-methyl-pyridin-3-ylmethyl)piperidin-4-ylidene]-4,9-dihydro-1-thia-benzo[f]azulen-10-one or ketotifen at the concentration of 01, 1, 10 or 100 μM for 1 hour and subsequently stimulated with antigen TNP-BSA (10 ng/ml) for 6 h. Cytokine levels in the cell free supernatant were determined by ELISA. As shown in FIG. 4, treatment of mast cells with 4-[1-(5-methyl-pyridin-3-ylmethyl)piperidin-4-ylidene]-4,9-dihydro-1-thia-benzo[f]azulen-10-one was found to significantly reduce cytokine IL-6 production by mast cells and was even more effective than ketotifen at some of the equivalent concentrations used.

The results provided herein demonstrates that (1): 4-[1-(5-methyl-pyridin-3-ylmethyl)piperidin-4-ylidene]-4,9-dihydro-1-thia-benzo[f]azulen-10-one blocks allergen-induced late-phase allergic inflammation in vivo; (2): 4-[1-(5-methyl-pyridin-3-ylmethyl)piperidin-4-ylidene]-4,9-dihydro-1-thia-benzo[f]azulen-10-one inhibits allergen-induced passive cutaneous anaphylaxis in vivo; and (3): 4-[1-(5-methyl-pyridin-3-ylmethyl)piperidin-4-ylidene]-4,9-dihydro-1-thia-benzo[f]azulen-10-one inhibits allergen-induced cytokine IL-6 production by mast cells in vitro.

Example 9

Inhibition of eosinophil proliferation in vitro by 4-[1-(5-methyl-pyridin-3-ylmethyl)piperidin-4-ylidene]-4,9-dihydro-1-thia-benzo[f]azulen-10-one Mouse bone marrow derived eosinophils ($1 \times 10^5$ cells/well) were seeded in 96 well plates in triplicate and were cultured with IL-5 (50 ng/ml). Eosinophils were treated with 4-[1-(5-methyl-pyridin-3-ylmethyl)piperidin-4-ylidene]-4,9-dihydro-1-thia-benzo[f]azulen-10-one (Compound A) or ketotifen for 1 hour. Cells were then pulsed with 0.5 μCi of $^3$H-thymidine for 18 hours. Cells were harvested to glass fiber paper using a suction manifold and washed extensively to eliminate unincorporated thymidine. Fiber paper was dried and added to vials with 2.5 ml of scintillation fluid (Ecolite). Thymidine incorporation was measured on a Wallac beta counter.

Figure 5:
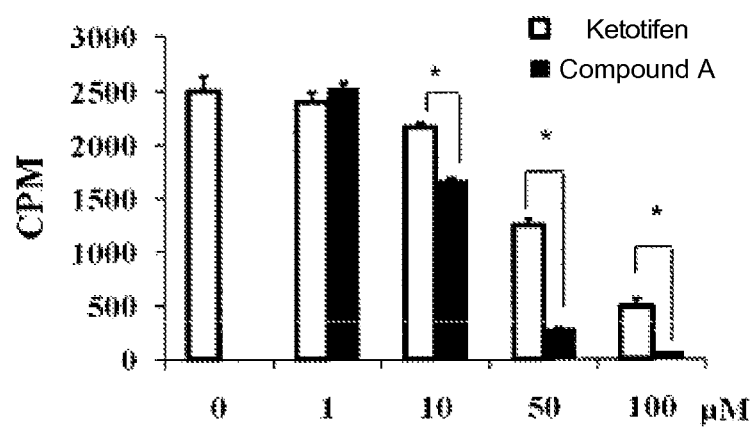
FIG. 5 depicts a bar graph illustrating inhibition of eosinophil proliferation in vitro by 4-[1-(5-methyl-pyridin-3-ylmethyl)piperidin-4-ylidene]-4,9-dihydro-1-thia-benzo[f]azulen-10-one (Compound A) and ketotifen. Asterix denotes statistical significance between the two groups.

The incorporation of $^3$H-thymidine (eosinophil proliferation) was quantified by liquid scintillation counting (CPM). Treatment with 4-[1-(5-methyl-pyridin-3-ylmethyl)piperidin-4-ylidene]-4,9-dihydro-1-thia-benzo[f]azulen-10-one or ketotifen dose-dependently reduced thymidine incorporation. These results suggest that 4-[1-(5-methyl-pyridin-3-ylmethyl)piperidin-4-ylidene]-4,9-dihydro-1-thia-benzo[f]azulen-10-one and ketotifen inhibit eosinophil proliferation. Importantly, 4-[1-(5-methyl-pyridin-3-ylmethyl)piperidin-4-ylidene]-4,9-dihydro-1-thia-benzo[f]azulen-10-one demonstrated significantly stronger inhibition on eosinophil proliferation than ketotifen did (*, $p<0.01$, n=3 experiments) as shown in FIG. 5.

The embodiments and the examples described herein are exemplary and not intended to be limiting in describing the full scope of compositions and methods of the present technology. Equivalent changes, modifications and variations of some embodiments, materials, compositions and methods can be made within the scope of the present technology, with substantially similar results.

What is claimed is:
1. A selective anti-allergy benzocycloheptathiophene derivative compound of Formula I:

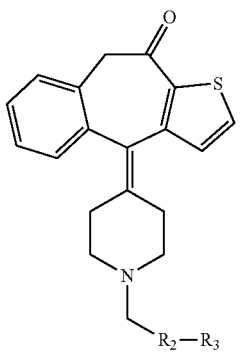

Formula I or a pharmaceutically acceptable salt, solvate or prodrug thereof, wherein $R_2$ is pyridine;

$R_3$ is each independently, hydrogen, halo, OH, —CN, —NO$_2$, —N=O, —NHOQ$_1$, —OQ$_1$, —SOQ$_1$, —SO$_2$Q$_1$, —SON(Q$_1$)$_2$, —SO$_2$N(Q$_1$)$_2$, —N(Q$_1$)$_2$, —C(O)OQ$_1$, —C(O)Q$_1$, —C(O)N(Q$_1$)$_2$, —C(=NQ$_1$)NQ$_1$-, —NQ$_1$C(=NQ$_1$)NQ$_1$-, —C(O)N(Q$_1$)(OQ$_1$), —N(Q$_1$)C(O)-Q$_1$, —N(Q$_1$)C(O)N(Q$_1$)$_2$, —N(Q$_1$)C(O)O-Q$_1$, —N(Q$_1$)SO$_2$Q$_1$, —N(Q$_1$)SOQ$_1$, C$_{1-8}$ alkyl, C$_{2-8}$ alkenyl, C$_{2-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, or heteroaralkyl, wherein each C$_{1-8}$ alkyl, C$_{2-8}$ alkenyl, C$_{2-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, or C$_{4-10}$ heteroaralkyl, optionally substituted with 1-3 substituents independently selected from Q$_1$ or Q$_2$;

each Q$_1$ is independently hydrogen, C$_{1-8}$ alkyl, C$_{2-8}$ alkenyl, alkoxy, alkenoxy, C$_{4-10}$ cycloalkyl, C$_{4-10}$ aryl, C$_{4-10}$ arylalkyl, aralkyloxy, C$_{4-10}$ heterocyclic, or C$_{4-10}$ heteroaryl ring, each optionally including 1-3 substituents independently selected from Q$_2$;

each Q$_2$ is halo, haloalkyl, oxo, oxime, azido, amino, amido, cyano, CN, NO$_2$, CF$_3$, OCF$_3$, OH, —COOH or C$_1$-C$_4$ alkyl optionally substituted with 1-3 of halo, oxo, oxime, —CN, —NO$_2$, —CF$_3$, —OCF$_3$, —OH, —SH, —S(O)$_3$H, —NH$_2$, or —COOH.

2. The selective anti-allergy benzocycloheptathiophene derivative compound according to claim 1, wherein R$_2$ is selected from:

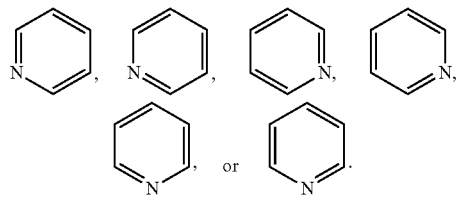

3. The selective anti-allergy benzocycloheptathiophene derivative compound according to claim 1, wherein R$_3$ is each independently selected from H, C$_{1-8}$ alkyl, C$_{1-8}$ alkenyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, or C$_{4-10}$ heteroaralkyl.

4. The selective anti-allergy benzocycloheptathiophene derivative compound according to claim 1, wherein R$_3$ is H or C$_{1-12}$ alkyl.

5. The selective anti-allergy benzocycloheptathiophene derivative compound according to claim 1, wherein R$_3$ is H, methyl, ethyl, propyl, isopropyl, butyl, isobutyl, hexyl, 2-ethylpropyl, and cyclohexyl.

6. The selective anti-allergy benzocycloheptathiophene derivative compound according to claim 1, wherein R$_3$ is H or methyl.

7. A selective anti-allergy benzocycloheptathiophene derivative compound of Formula Ia:

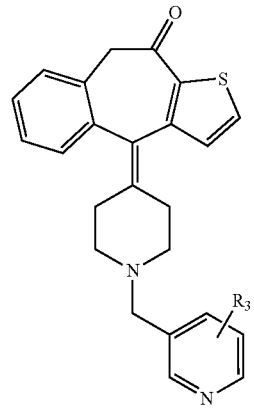

Formula Ia or a pharmaceutically acceptable salt, solvate or prodrug thereof, wherein R$_3$ is each independently, hydrogen, halo, OH, —CN, —NO$_2$, —N=O, —NHOQ$_1$, —OQ$_1$, —SOQ$_1$, —SO$_2$Q$_1$, —SON(Q$_1$)$_2$, —SO$_2$N(Q$_1$)$_2$, —N(Q$_1$)$_2$, —C(O)OQ$_1$, —C(O)Q$_1$, —C(O)N(Q$_1$)$_2$, —C(=NQ$_1$)NQ$_1$-, —NQ$_1$C(=NQ$_1$)NQ$_1$-, —C(O)N(Q$_1$)(OQ$_1$), —N(Q$_1$)C(O)-Q$_1$-N(Q$_1$)C(O)N(Q$_1$)$_2$, —N(Q$_1$)C(O)O-Q$_1$-N(Q$_1$)SO$_2$Q$_1$, —N(Q$_1$)SOQ$_1$, C$_{1-8}$ alkyl, C$_{2-8}$ alkenyl, C$_{2-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, or heteroaralkyl, wherein each C$_{1-8}$ alkyl, C$_{2-8}$ alkenyl, C$_{2-8}$ alkynyl, alkoxy, alkenoxy, C$_{4-10}$ cycloalkyl, C$_{4-10}$ heterocycloalkyl, C$_{4-10}$ aryl, C$_{4-10}$ aralkyl, aralkyloxy, C$_{4-10}$ heteroaryl, or C$_{4-10}$-heteroaralkyl, optionally substituted with 1-3 substituents independently selected from Q$_1$ or Q$_2$;

each Q$_1$ is independently hydrogen, C$_{1-8}$ alkyl, C$_{2-8}$ alkenyl, alkoxy, alkenoxy, C$_{4-10}$ cycloalkyl, C$_{4-10}$ aryl, C$_{4-10}$ arylalkyl, aralkyloxy, C$_{4-10}$ heterocyclic, or C$_{4-10}$ heteroaryl ring, each optionally including 1-3 substituents independently selected from Q$_2$;

each Q$_2$ is halo, haloalkyl, oxo, oxime, azido, amino, amido, cyano, CN, NO$_2$, CF$_3$, OCF$_3$, OH, —COOH or C$_1$-C$_4$ alkyl optionally substituted with 1-3 of halo, oxo, oxime, —CN, —NO$_2$, —CF$_3$, —OCF$_3$, —OH, —SH, —S(O)$_3$H, —NH$_2$, or —COOH.

8. The selective anti-allergy benzocycloheptathiophene derivative compound according to claim 7, wherein R$_3$ is H or C$_{1-8}$ alkyl.

9. The selective anti-allergy benzocycloheptathiophene derivative compound according to claim 7, wherein R$_3$ is H, methyl, ethyl, propyl, isopropyl, butyl, isobutyl, hexyl, 2-ethylpropyl, and cyclohexyl.

10. The selective anti-allergy benzocycloheptathiophene derivative compound according to claim 7, wherein $R_3$ is H or methyl.

11. A selective anti-allergy benzocycloheptathiophene derivative compound comprising at least one selected from:

1

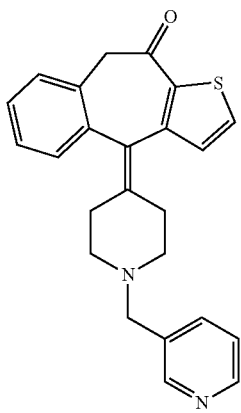 [SMILES: O=C1Cc2ccccc2C(=C2CCN(Cc3cccnc3)CC2)c2ccsc21]

$C_{24}H_{22}N_2OS$
4-(1-Pyridin-3-ylmethyl-piperidin-4-ylidene)-
4,9-dihydro-1-thia-benzo[f]azulen-10-one

2

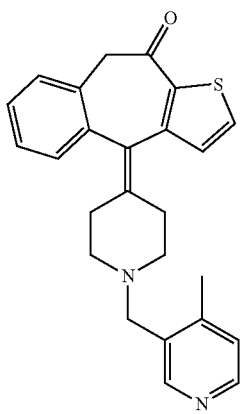 [SMILES: Cc1ccncc1CN1CCC(=C2c3ccccc3CC(=O)c3sccc32)CC1]

$C_{25}H_{24}N_2OS$
4-[1-(4-Methyl-pyridin-3-ylmethyl)-piperidin-4-ylidene]-
4,9-dihydro-1-thia-benzo[f]azulen-10-one

3

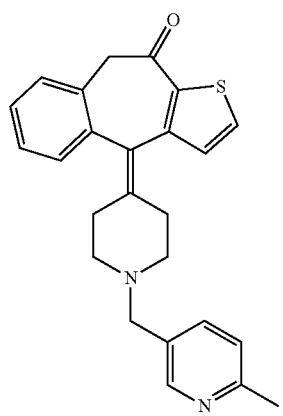 [SMILES: Cc1ccc(CN2CCC(=C3c4ccccc4CC(=O)c4sccc43)CC2)cn1]

$C_{25}H_{24}N_2OS$
4-[1-(6-Methyl-pyridin-3-ylmethyl)-piperidin-4-ylidene]-
4,9-dihydro-1-thia-benzo[f]azulen-10-one

4

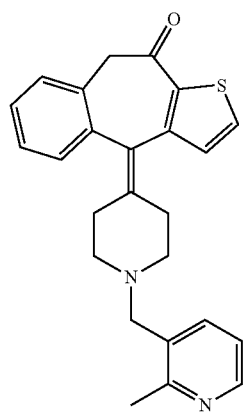 [SMILES: Cc1ncccc1CN1CCC(=C2c3ccccc3CC(=O)c3sccc32)CC1]

$C_{25}H_{24}N_2OS$
4-[1-(2-Methyl-pyridin-3-ylmethyl)-piperidin-4-ylidene]-
4,9-dihydro-1-thia-benzo[f]azulen-10-one

5

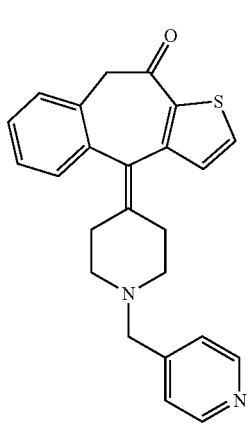 [SMILES: O=C1Cc2ccccc2C(=C2CCN(Cc3ccncc3)CC2)c2ccsc21]

$C_{24}H_{22}N_2OS$
4-(1-Pyridin-4-ylmethyl-piperidin-4-ylidene)-
4,9-dihydro-1-thia-benzo[f]azulen-10-one

6

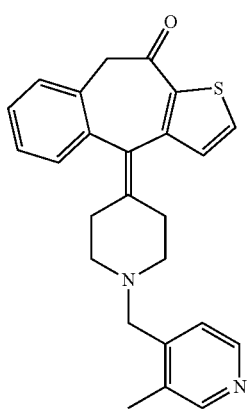 [SMILES: Cc1cnccc1CN1CCC(=C2c3ccccc3CC(=O)c3sccc32)CC1]

$C_{25}H_{24}N_2OS$
4-[1-(3-Methyl-pyridin-4-ylmethyl)-piperidin-4-ylidene]-
4,9-dihydro-1-thia-benzo[f]azulen-10-one

7

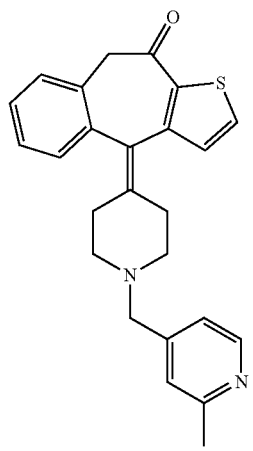 [SMILES: Cc1cc(CN2CCC(=C3c4ccccc4CC(=O)c4sccc43)CC2)ccn1]

C$_{25}$H$_{24}$N$_2$OS
4-[1-(2-Methyl-pyridin-4-ylmethyl)-piperidin-4-ylidene]-
4,9-dihydro-1-thia-benzo[f]azulen-10-one

8

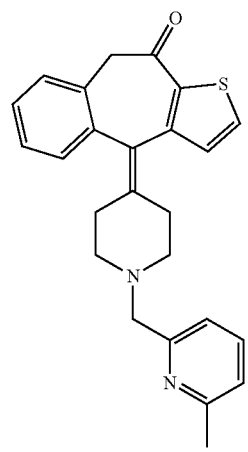 [SMILES: Cc1cccc(CN2CCC(=C3c4ccccc4CC(=O)c4sccc43)CC2)n1]

C$_{25}$H$_{24}$N$_2$OS
4-[1-(6-Methyl-pyridin-2-ylmethyl)-piperidin-4-ylidene]-
4,9-dihydro-1-thia-benzo[f]azulen-10-one

9

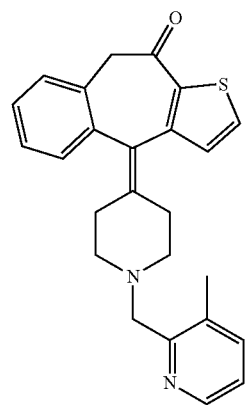 [SMILES: Cc1cccnc1CN1CCC(=C2c3ccccc3CC(=O)c3sccc32)CC1]

C$_{25}$H$_{24}$N$_2$OS
4-[1-(3-Methyl-pyridin-2-ylmethyl)-piperidin-4-ylidene]-
4,9-dihydro-1-thia-benzo[f]azulen-10-one

10

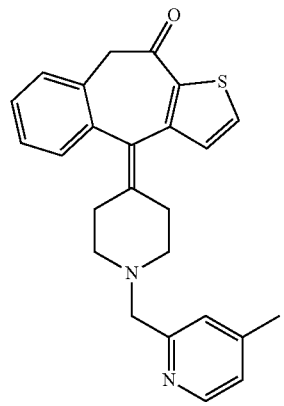 [SMILES: Cc1ccnc(CN2CCC(=C3c4ccccc4CC(=O)c4sccc43)CC2)c1]

C$_{25}$H$_{24}$N$_2$OS
4-[1-(4-Methyl-pyridin-2-ylmethyl)-piperidin-4-ylidene]-
4,9-dihydro-1-thia-benzo[f]azulen-10-one

11

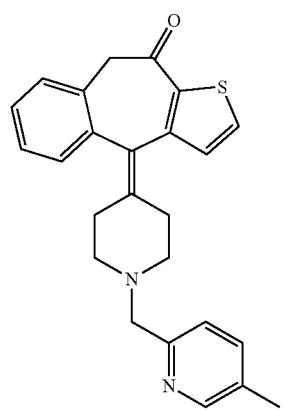 [SMILES: Cc1ccc(CN2CCC(=C3c4ccccc4CC(=O)c4sccc43)CC2)nc1]

C$_{25}$H$_{24}$N$_2$OS
4-[1-(5-Methyl-pyridin-2-ylmethyl)-piperidin-4-ylidene]-
4,9-dihydro-1-thia-benzo[f]azulen-10-one

12

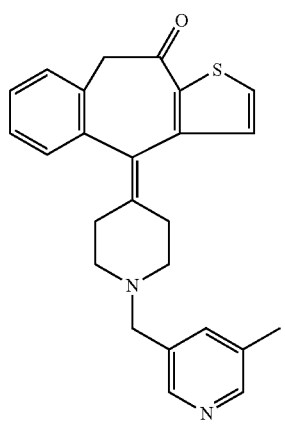 [SMILES: Cc1cncc(CN2CCC(=C3c4ccccc4CC(=O)c4sccc43)CC2)c1]

Molecular Formula = C$_{25}$H$_{24}$N$_2$OS
4-[1-(5-Methyl-pyridin-3-ylmethyl)-piperidin-4-ylidene]-
4,9-dihydro-1-thia-benzo[f]azulen-10-one.

12. The selective anti-allergy benzocycloheptathiophene derivative compound according to claim 1, wherein said compound is present as a fumarate salt.

13. A pharmaceutical composition comprising the selective anti-allergy benzocycloheptathiophene derivative compound according to claim 1 and a pharmaceutically acceptable carrier, vehicle or excipient.

14. A pharmaceutical composition comprising a therapeutically effective amount of the selective anti-allergy benzocycloheptathiophene derivative compound according to claim 11, and a pharmaceutically acceptable carrier, vehicle or excipient.

15. The pharmaceutical composition according to claim 14, wherein said benzocycloheptathiophene derivative compound is 4-[1-(5-methyl-pyridin-3-ylmethyl)-piperidin-4-ylidene]-4,9-dihydro-1-thia-benzo[f]azulen-10-one, and a pharmaceutically acceptable carrier, vehicle or excipient.

16. A pharmaceutical unit-dose composition comprising the selective anti-allergy benzocycloheptathiophene derivative compound according to claim 11 in an amount ranging from about 1 to about 10 milligrams, and a pharmaceutically acceptable carrier, vehicle or excipient.

17. The pharmaceutical unit-dose composition according to claim 16, wherein said benzocycloheptathiophene derivative compound is 4-[1-(5-methyl-pyridin-3-ylmethyl)-piperidin-4-ylidene]-4,9-dihydro-1-thia-benzo[f]azulen-10-one.

18. An ophthalmic composition for a treatment of an allergic condition of an eye, the composition comprising the benzocycloheptathiophene derivative compound according to claim 1 and an ophthalmic acceptable carrier, vehicle or excipient.

19. An ophthalmic composition for a treatment of an allergic condition of an eye, the composition comprising the benzocycloheptathiophene derivative compound according to claim 11, and an ophthalmic acceptable carrier, vehicle or excipient.

20. The ophthalmic composition according to claim 19, wherein the benzocycloheptathiophene derivative compound is present in the ophthalmic composition in an amount from about 0.01% to about 0.1% (wt/vol.).

21. The ophthalmic composition according to claim 20, wherein the benzocycloheptathiophene derivative compound comprises 4-[1-(5-methyl-pyridin-3-ylmethyl)-piperidin-4-ylidene]-4,9-dihydro-1-thia-benzo[f]azulen-10-one.

* * * * *